(12) United States Patent
Matthews et al.

(10) Patent No.: US 8,968,396 B2
(45) Date of Patent: Mar. 3, 2015

(54) INTRAOCULAR LENS DELIVERY SYSTEMS AND METHODS OF USE

(71) Applicant: PowerVision, Inc., Belmont, CA (US)

(72) Inventors: Gregory Vinton Matthews, San Francisco, CA (US); Terah Whiting Smiley, San Francisco, CA (US); John A. Scholl, San Ramon, CA (US)

(73) Assignee: PowerVision, Inc., Belmont, CA (US)

( * ) Notice: Subject to any disclaimer, the term of this patent is extended or adjusted under 35 U.S.C. 154(b) by 0 days.

(21) Appl. No.: 13/835,876

(22) Filed: Mar. 15, 2013

(65) Prior Publication Data

US 2014/0012277 A1    Jan. 9, 2014

Related U.S. Application Data

(63) Continuation-in-part of application No. 12/178,565, filed on Jul. 23, 2008.

(60) Provisional application No. 60/951,439, filed on Jul. 23, 2007, provisional application No. 61/613,929, filed on Mar. 21, 2012.

(51) Int. Cl.
*A61F 2/16*    (2006.01)

(52) U.S. Cl.
CPC ............... *A61F 2/1675* (2013.01); *A61F 2/167* (2013.01); *A61F 2/1678* (2013.01)
USPC ....................................... 623/6.12

(58) Field of Classification Search
USPC ................. 606/107; 623/6.12, 6.11, 905–907
See application file for complete search history.

(56) References Cited

U.S. PATENT DOCUMENTS

| | | |
|---|---|---|
| 4,111,995 A | 9/1978 | Nelson |
| 4,251,887 A | 2/1981 | Anis |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,600,004 A | 7/1986 | Lopez et al. |
| 4,604,295 A | 8/1986 | Humphreys |

(Continued)

FOREIGN PATENT DOCUMENTS

| | | |
|---|---|---|
| CN | 101277659 A | 10/2008 |
| EP | 0898972 A2 | 3/1999 |

(Continued)

OTHER PUBLICATIONS

Baughman et al., "Negative poisson's ratios for extreme states of matter," Science, vol. 288, pp. 2018-2022, Jun. 16, 2000.

(Continued)

*Primary Examiner* — Ashley Fishback
(74) *Attorney, Agent, or Firm* — Shay Glenn LLP

(57) ABSTRACT

Intraocular lens delivery devices and methods of use.

35 Claims, 17 Drawing Sheets

(56) References Cited

U.S. PATENT DOCUMENTS

| | | |
|---|---|---|
| 4,615,701 A | 10/1986 | Woods |
| 4,620,954 A | 11/1986 | Singer et al. |
| 4,681,102 A | 7/1987 | Bartell |
| 4,685,921 A | 8/1987 | Peyman |
| 4,685,922 A | 8/1987 | Peyman |
| 4,693,717 A | 9/1987 | Michelson |
| 4,702,244 A | 10/1987 | Mazzocco |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,747,404 A | 5/1988 | Jampel et al. |
| 4,763,650 A | 8/1988 | Hauser |
| 4,764,423 A | 8/1988 | Yamaguchi et al. |
| 4,765,329 A | 8/1988 | Cumming et al. |
| 4,781,719 A | 11/1988 | Kelman |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,819,631 A | 4/1989 | Poley |
| 4,834,094 A | 5/1989 | Patton et al. |
| 4,836,201 A | 6/1989 | Patton et al. |
| 4,842,601 A | 6/1989 | Smith |
| 4,848,343 A | 7/1989 | Wallsten et al. |
| 4,862,885 A | 9/1989 | Cumming |
| 4,880,000 A | 11/1989 | Holmes et al. |
| 4,888,012 A | 12/1989 | Horn et al. |
| 4,892,543 A | 1/1990 | Turley |
| 4,902,293 A | 2/1990 | Feaster |
| 4,906,247 A | 3/1990 | Fritch |
| 4,911,158 A | 3/1990 | Weatherly |
| 4,911,714 A | 3/1990 | Poley |
| 4,913,536 A | 4/1990 | Barnea |
| 4,917,680 A | 4/1990 | Poley |
| 4,919,130 A | 4/1990 | Stoy et al. |
| 4,919,151 A | 4/1990 | Grubbs et al. |
| 4,932,966 A | 6/1990 | Christie et al. |
| 4,934,363 A | 6/1990 | Smith et al. |
| 4,946,469 A | 8/1990 | Sarfarazi |
| 4,950,289 A | 8/1990 | Krasner |
| 4,955,889 A | 9/1990 | Van Gent |
| 4,963,148 A | 10/1990 | Sulc et al. |
| 4,988,352 A | 1/1991 | Poley |
| 4,994,082 A | 2/1991 | Richards et al. |
| 4,995,879 A | 2/1991 | Dougherty |
| 4,995,880 A | 2/1991 | Galib |
| 5,007,913 A | 4/1991 | Dulebohn et al. |
| 5,015,254 A | 5/1991 | Greite |
| 5,026,393 A | 6/1991 | Mackool |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,098,439 A | 3/1992 | Hill et al. |
| 5,100,410 A | 3/1992 | Dulebohn |
| 5,123,905 A | 6/1992 | Kelman |
| 5,145,884 A | 9/1992 | Yamamoto et al. |
| 5,145,935 A | 9/1992 | Hayashi |
| 5,152,789 A | 10/1992 | Willis |
| 5,171,241 A | 12/1992 | Buboltz et al. |
| 5,171,266 A | 12/1992 | Wiley et al. |
| 5,176,686 A | 1/1993 | Poley |
| 5,190,552 A | 3/1993 | Kelman |
| 5,200,430 A | 4/1993 | Federman |
| 5,201,763 A | 4/1993 | Brady et al. |
| 5,203,788 A | 4/1993 | Wiley |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,304,182 A | 4/1994 | Rheinish et al. |
| 5,326,347 A | 7/1994 | Cumming |
| 5,354,333 A | 10/1994 | Kammann et al. |
| 5,391,590 A | 2/1995 | Gerace et al. |
| 5,405,386 A | 4/1995 | Rheinish et al. |
| 5,425,734 A | 6/1995 | Blake |
| 5,443,506 A | 8/1995 | Garabet |
| 5,444,106 A | 8/1995 | Zhou et al. |
| 5,444,135 A | 8/1995 | Cheradame et al. |
| 5,452,932 A | 9/1995 | Griffin |
| 5,468,246 A | 11/1995 | Blake |
| 5,474,562 A | 12/1995 | Orchowski et al. |
| 5,476,514 A | 12/1995 | Cumming |
| 5,489,302 A | 2/1996 | Skottun |
| 5,494,484 A | 2/1996 | Feingold |
| 5,496,328 A | 3/1996 | Nakajima et al. |
| 5,496,366 A | 3/1996 | Cumming |
| 5,499,987 A | 3/1996 | Feingold |
| 5,506,300 A | 4/1996 | Ward et al. |
| 5,512,609 A | 4/1996 | Yang |
| 5,549,614 A | 8/1996 | Tunis |
| 5,556,400 A | 9/1996 | Tunis |
| 5,562,676 A | 10/1996 | Brady et al. |
| 5,578,081 A | 11/1996 | McDonald |
| 5,582,613 A | 12/1996 | Brady et al. |
| 5,584,304 A | 12/1996 | Brady |
| 5,585,049 A | 12/1996 | Grisoni et al. |
| 5,593,436 A | 1/1997 | Langerman |
| 5,607,433 A | 3/1997 | Polla et al. |
| 5,607,472 A | 3/1997 | Thompson |
| 5,616,148 A | 4/1997 | Eagles et al. |
| 5,620,450 A | 4/1997 | Eagles et al. |
| 5,628,795 A | 5/1997 | Langerman |
| 5,633,504 A | 5/1997 | Collins et al. |
| 5,643,276 A | 7/1997 | Zaleski |
| 5,653,715 A | 8/1997 | Reich et al. |
| 5,665,822 A | 9/1997 | Bitler et al. |
| 5,674,282 A | 10/1997 | Cumming |
| 5,676,669 A | 10/1997 | Colvard |
| 5,697,973 A | 12/1997 | Peyman et al. |
| 5,702,400 A | 12/1997 | Brown et al. |
| 5,702,402 A | 12/1997 | Brady |
| 5,702,441 A | 12/1997 | Zhou |
| 5,716,364 A | 2/1998 | Makker et al. |
| 5,728,102 A * | 3/1998 | Feingold et al. .............. 606/107 |
| 5,735,858 A | 4/1998 | Makker et al. |
| 5,766,182 A | 6/1998 | McDonald |
| 5,772,666 A | 6/1998 | Feingold et al. |
| 5,774,273 A | 6/1998 | Bornhorst |
| 5,776,138 A | 7/1998 | Vidal et al. |
| 5,776,191 A | 7/1998 | Mazzocco |
| 5,776,192 A | 7/1998 | McDonald |
| 5,800,442 A | 9/1998 | Wolf et al. |
| 5,803,925 A | 9/1998 | Yang et al. |
| 5,810,834 A | 9/1998 | Heyman |
| 5,843,188 A | 12/1998 | McDonald |
| 5,860,984 A | 1/1999 | Chambers et al. |
| 5,868,751 A | 2/1999 | Feingold |
| 5,873,879 A | 2/1999 | Figueroa et al. |
| 5,876,440 A | 3/1999 | Feingold |
| 5,891,931 A | 4/1999 | Leboeuf et al. |
| 5,919,197 A | 7/1999 | McDonald |
| 5,921,989 A | 7/1999 | Deacon et al. |
| 5,928,282 A | 7/1999 | Nigam |
| 5,941,886 A | 8/1999 | Feingold |
| 5,944,725 A | 8/1999 | Cicenas et al. |
| 5,947,974 A | 9/1999 | Brady et al. |
| 5,947,975 A | 9/1999 | Kikuchi et al. |
| 5,947,976 A | 9/1999 | Van Noy et al. |
| 5,964,802 A | 10/1999 | Anello et al. |
| 5,976,150 A | 11/1999 | Copeland |
| 5,984,962 A | 11/1999 | Anello et al. |
| 6,001,107 A | 12/1999 | Feingold |
| 6,010,510 A | 1/2000 | Brown et al. |
| 6,013,101 A | 1/2000 | Israel |
| 6,015,842 A | 1/2000 | LeBoeuf et al. |
| 6,022,358 A | 2/2000 | Wolf et al. |

(56) References Cited

U.S. PATENT DOCUMENTS

| | | | |
|---|---|---|---|
| 6,048,348 | A | 4/2000 | Chambers et al. |
| 6,059,791 | A | 5/2000 | Chambers |
| 6,074,397 | A | 6/2000 | Chambers et al. |
| 6,102,539 | A | 8/2000 | Tucker |
| 6,117,171 | A | 9/2000 | Skottun |
| 6,124,980 | A | 9/2000 | Cerbell |
| 6,129,733 | A | 10/2000 | Brady et al. |
| 6,139,576 | A | 10/2000 | Doyle et al. |
| 6,143,000 | A | 11/2000 | Feingold |
| 6,143,001 | A | 11/2000 | Brown et al. |
| 6,160,084 | A | 12/2000 | Langer et al. |
| 6,176,878 | B1 | 1/2001 | Gwon et al. |
| 6,179,843 | B1 | 1/2001 | Weiler |
| 6,180,687 | B1 | 1/2001 | Hammer et al. |
| 6,188,526 | B1 | 2/2001 | Sasaya et al. |
| 6,190,410 | B1 | 2/2001 | Lamielle et al. |
| 6,195,807 | B1 | 3/2001 | Chou |
| 6,197,059 | B1 | 3/2001 | Cumming |
| 6,217,612 | B1 | 4/2001 | Woods |
| 6,225,367 | B1 | 5/2001 | Chaouk et al. |
| 6,229,641 | B1 | 5/2001 | Kosaka |
| 6,241,737 | B1 | 6/2001 | Feingold |
| 6,248,111 | B1 | 6/2001 | Glick et al. |
| 6,251,114 | B1 | 6/2001 | Farmer et al. |
| 6,280,449 | B1 | 8/2001 | Blake |
| 6,283,975 | B1 | 9/2001 | Glick et al. |
| 6,283,976 | B1 | 9/2001 | Portney |
| 6,299,641 | B1 | 10/2001 | Woods |
| 6,302,911 | B1 | 10/2001 | Hanna |
| 6,312,433 | B1 | 11/2001 | Butts et al. |
| 6,322,589 | B1 | 11/2001 | Cumming |
| 6,334,862 | B1 | 1/2002 | Vidal et al. |
| 6,336,932 | B1 | 1/2002 | Figueroa et al. |
| 6,342,073 | B1 | 1/2002 | Cumming et al. |
| 6,348,437 | B1 | 2/2002 | Avery et al. |
| 6,371,960 | B2 | 4/2002 | Heyman et al. |
| 6,387,101 | B1 | 5/2002 | Butts et al. |
| 6,387,126 | B1 | 5/2002 | Cumming |
| 6,388,043 | B1 | 5/2002 | Langer et al. |
| 6,398,789 | B1 | 6/2002 | Capetan |
| 6,406,481 | B2 | 6/2002 | Feingold et al. |
| 6,406,494 | B1 | 6/2002 | Laguette et al. |
| 6,413,262 | B2 | 7/2002 | Saishin et al. |
| 6,423,094 | B1 | 7/2002 | Sarfarazi |
| 6,436,092 | B1 | 8/2002 | Peyman |
| 6,443,985 | B1 | 9/2002 | Woods |
| 6,447,520 | B1 | 9/2002 | Ott et al. |
| 6,450,642 | B1 | 9/2002 | Jethmalani et al. |
| 6,464,725 | B2 | 10/2002 | Skotton |
| 6,468,282 | B2 | 10/2002 | Kikuchi et al. |
| 6,471,708 | B2 | 10/2002 | Green |
| 6,488,708 | B2 | 12/2002 | Sarfarazi |
| 6,491,697 | B1 | 12/2002 | Clark et al. |
| 6,493,151 | B2 | 12/2002 | Schachar |
| 6,497,708 | B1 | 12/2002 | Cumming |
| 6,503,275 | B1 | 1/2003 | Cumming |
| 6,503,276 | B2 | 1/2003 | Lang et al. |
| 6,506,195 | B2 | 1/2003 | Chambers et al. |
| 6,517,577 | B1 | 2/2003 | Callahan et al. |
| 6,537,283 | B2 | 3/2003 | Van Noy |
| 6,551,354 | B1 | 4/2003 | Ghazizadeh et al. |
| 6,552,860 | B1 | 4/2003 | Alden |
| 6,554,859 | B1 | 4/2003 | Lang et al. |
| 6,585,768 | B2 | 7/2003 | Hamano et al. |
| 6,589,550 | B1 | 7/2003 | Hodd et al. |
| 6,592,621 | B1 | 7/2003 | Domino |
| 6,599,317 | B1 | 7/2003 | Weinschenk, III et al. |
| 6,601,956 | B1 | 8/2003 | Jean et al. |
| 6,605,093 | B1 | 8/2003 | Blake |
| 6,610,350 | B2 | 8/2003 | Suzuki et al. |
| 6,616,691 | B1 | 9/2003 | Tran |
| 6,616,692 | B1 | 9/2003 | Glick et al. |
| 6,638,304 | B2 | 10/2003 | Azar |
| 6,638,305 | B2 | 10/2003 | Laguette |
| 6,638,306 | B2 | 10/2003 | Cumming |
| 6,645,245 | B1 | 11/2003 | Preussner |
| 6,645,246 | B1 | 11/2003 | Weinschenk, III et al. |
| 6,656,223 | B2 | 12/2003 | Brady |
| 6,660,035 | B1 | 12/2003 | Lang et al. |
| 6,692,525 | B2 | 2/2004 | Brady et al. |
| 6,695,881 | B2 | 2/2004 | Peng et al. |
| 6,709,108 | B2 | 3/2004 | Levine et al. |
| 6,712,848 | B1 | 3/2004 | Wolf et al. |
| 6,723,104 | B2 | 4/2004 | Ott |
| 6,730,123 | B1 | 5/2004 | Klopotek |
| 6,733,507 | B2 | 5/2004 | McNicholas et al. |
| 6,743,388 | B2 | 6/2004 | Sridharan et al. |
| 6,749,632 | B2 | 6/2004 | Sandstedt et al. |
| 6,749,634 | B2 | 6/2004 | Hanna |
| 6,786,934 | B2 | 9/2004 | Zadno-Azizi et al. |
| 6,818,158 | B2 | 11/2004 | Pham et al. |
| 6,827,738 | B2 | 12/2004 | Willis et al. |
| 6,836,374 | B2 | 12/2004 | Esch et al. |
| 6,860,601 | B2 | 3/2005 | Shadduck |
| 6,878,320 | B1 | 4/2005 | Alderson et al. |
| 6,884,261 | B2 | 4/2005 | Zadno-Azizi et al. |
| 6,899,732 | B2 | 5/2005 | Zadno-Azizi et al. |
| 6,899,850 | B2 | 5/2005 | Haywood et al. |
| 6,914,247 | B2 | 7/2005 | Duggan et al. |
| 6,921,405 | B2 | 7/2005 | Feingold et al. |
| 6,923,815 | B2 | 8/2005 | Brady et al. |
| 6,926,736 | B2 | 8/2005 | Peng et al. |
| 6,935,743 | B2 | 8/2005 | Shadduck |
| 6,949,093 | B1 | 9/2005 | Peyman |
| 6,966,649 | B2 | 11/2005 | Shadduck |
| 6,969,403 | B2 | 11/2005 | Peng et al. |
| 7,001,374 | B2 | 2/2006 | Peyman |
| 7,014,641 | B2 | 3/2006 | Kobayashi et al. |
| 7,060,094 | B2 | 6/2006 | Shahinpoor et al. |
| 7,068,439 | B2 | 6/2006 | Esch et al. |
| 7,070,276 | B2 | 7/2006 | Koretz |
| 7,074,227 | B2 | 7/2006 | Portney |
| 7,122,053 | B2 | 10/2006 | Esch |
| 7,144,423 | B2 | 12/2006 | McDonald |
| 7,156,854 | B2 | 1/2007 | Brown et al. |
| 7,217,288 | B2 | 5/2007 | Esch et al. |
| 7,241,312 | B2 | 7/2007 | Lai et al. |
| 7,247,168 | B2 | 7/2007 | Esch et al. |
| 7,247,689 | B2 | 7/2007 | Makker et al. |
| 7,261,737 | B2 | 8/2007 | Esch et al. |
| 7,264,351 | B2 | 9/2007 | Shadduck |
| 7,276,619 | B2 | 10/2007 | Kunzler et al. |
| 7,278,739 | B2 | 10/2007 | Shadduck |
| 7,311,194 | B2 | 12/2007 | Jin et al. |
| 7,335,209 | B2 | 2/2008 | Meyer |
| 7,416,300 | B2 | 8/2008 | Wei et al. |
| 7,429,263 | B2 | 9/2008 | Vaquero et al. |
| 7,438,723 | B2 | 10/2008 | Esch |
| 7,453,646 | B2 | 11/2008 | Lo |
| 7,485,144 | B2 | 2/2009 | Esch |
| 7,494,505 | B2 | 2/2009 | Kappelhof et al. |
| 7,637,947 | B2 | 12/2009 | Smith et al. |
| 7,675,686 | B2 | 3/2010 | Lo et al. |
| 7,753,953 | B1 | 7/2010 | Yee |
| 7,759,408 | B2 | 7/2010 | Schorzman et al. |
| 7,763,069 | B2 | 7/2010 | Brady et al. |
| 7,776,088 | B2 | 8/2010 | Shadduck |
| 7,878,655 | B2 | 2/2011 | Salvati et al. |
| 7,971,997 | B2 | 7/2011 | Hiramatsu et al. |
| 7,988,290 | B2 | 8/2011 | Campbell et al. |
| 7,988,292 | B2 | 8/2011 | Neal et al. |
| 7,988,293 | B2 | 8/2011 | Raymond et al. |
| 8,048,155 | B2 | 11/2011 | Shadduck |
| 8,158,712 | B2 | 4/2012 | Your |
| 8,162,927 | B2 | 4/2012 | Peyman |
| 8,241,355 | B2 | 8/2012 | Brady et al. |
| 8,246,631 | B2 | 8/2012 | Pynson |
| 8,303,656 | B2 | 11/2012 | Shadduck |
| 8,314,927 | B2 | 11/2012 | Choi et al. |
| 8,328,869 | B2 | 12/2012 | Smiley et al. |
| 8,361,145 | B2 | 1/2013 | Scholl et al. |
| 8,382,769 | B2 | 2/2013 | Inoue |
| 8,403,941 | B2 | 3/2013 | Peterson et al. |
| 8,425,599 | B2 | 4/2013 | Shadduck |

(56) References Cited

U.S. PATENT DOCUMENTS

| | | |
|---|---|---|
| 8,447,086 B2 | 5/2013 | Hildebrand et al. |
| 8,454,688 B2 | 6/2013 | Esch et al. |
| 8,475,526 B2 | 7/2013 | Pynson |
| 8,613,766 B2 | 12/2013 | Richardson et al. |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133167 A1 | 9/2002 | Harish et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0186868 A1 | 9/2004 | Kim |
| 2004/0193263 A1 | 9/2004 | Bryan |
| 2004/0230203 A1 | 11/2004 | Yaguchi |
| 2004/0267359 A1 | 12/2004 | Makker et al. |
| 2005/0021139 A1 | 1/2005 | Shadduck |
| 2005/0033308 A1 | 2/2005 | Callahan et al. |
| 2005/0038446 A1 | 2/2005 | Vanderbilt et al. |
| 2005/0049606 A1 | 3/2005 | Vaquero et al. |
| 2005/0080484 A1 | 4/2005 | Marmo et al. |
| 2005/0113911 A1 | 5/2005 | Peyman |
| 2005/0125000 A1 | 6/2005 | Tourrette et al. |
| 2005/0125055 A1 | 6/2005 | Deacon et al. |
| 2005/0125056 A1 | 6/2005 | Deacon et al. |
| 2005/0131535 A1 | 6/2005 | Woods |
| 2005/0143750 A1 | 6/2005 | Vaquero |
| 2005/0143751 A1 | 6/2005 | Makker et al. |
| 2005/0147735 A1 | 7/2005 | Lowery et al. |
| 2005/0149057 A1 | 7/2005 | Rathert |
| 2005/0165410 A1 | 7/2005 | Zadno-Azizi et al. |
| 2005/0222577 A1 | 10/2005 | Vaquero |
| 2005/0222578 A1 | 10/2005 | Vaquero |
| 2005/0222579 A1 | 10/2005 | Vaquero et al. |
| 2005/0251253 A1 | 11/2005 | Gross |
| 2005/0251254 A1 | 11/2005 | Brady et al. |
| 2005/0259221 A1 | 11/2005 | Marmo |
| 2005/0264756 A1 | 12/2005 | Esch |
| 2005/0283162 A1 | 12/2005 | Stratas |
| 2005/0283164 A1 | 12/2005 | Wu et al. |
| 2006/0020267 A1 | 1/2006 | Marmo |
| 2006/0020268 A1 | 1/2006 | Brady et al. |
| 2006/0069433 A1 | 3/2006 | Nun |
| 2006/0085013 A1 | 4/2006 | Dusek et al. |
| 2006/0097413 A1 | 5/2006 | Ghazizadeh et al. |
| 2006/0100703 A1 | 5/2006 | Evans et al. |
| 2006/0116763 A1 | 6/2006 | Simpson |
| 2006/0129129 A1 | 6/2006 | Smith |
| 2006/0134173 A1 | 6/2006 | Liu et al. |
| 2006/0135642 A1 | 6/2006 | Makker et al. |
| 2006/0142780 A1 | 6/2006 | Pynson et al. |
| 2006/0142781 A1 | 6/2006 | Pynson et al. |
| 2006/0158611 A1 | 7/2006 | Piers et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0027538 A1* | 2/2007 | Aharoni et al. ............... 623/6.12 |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0213817 A1 | 9/2007 | Esch et al. |
| 2007/0244561 A1 | 10/2007 | Ben Nun |
| 2007/0265636 A1 | 11/2007 | Huynh |
| 2008/0004699 A1 | 1/2008 | Ben Nun |
| 2008/0015689 A1 | 1/2008 | Esch et al. |
| 2008/0027537 A1 | 1/2008 | Gerlach et al. |
| 2008/0033449 A1 | 2/2008 | Cole et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0058830 A1 | 3/2008 | Cole et al. |
| 2008/0065096 A1 | 3/2008 | Kappelhof et al. |
| 2008/0071286 A1 | 3/2008 | Kobayashi et al. |
| 2008/0097460 A1 | 4/2008 | Boukhny et al. |
| 2008/0119865 A1 | 5/2008 | Meunier et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0200921 A1 | 8/2008 | Downer |
| 2008/0243247 A1 | 10/2008 | Poley et al. |
| 2008/0269887 A1 | 10/2008 | Cumming |
| 2008/0300680 A1 | 12/2008 | Joshua |
| 2008/0306587 A1 | 12/2008 | Your |
| 2009/0005865 A1 | 1/2009 | Smiley et al. |
| 2009/0018512 A1 | 1/2009 | Charles |
| 2009/0018548 A1 | 1/2009 | Charles |
| 2009/0024136 A1 | 1/2009 | Martin et al. |
| 2009/0030425 A1 | 1/2009 | Smiley et al. |
| 2009/0076602 A1 | 3/2009 | Ho et al. |
| 2009/0112313 A1 | 4/2009 | Mentak |
| 2009/0118739 A1 | 5/2009 | Kappelhof et al. |
| 2009/0124773 A1 | 5/2009 | Zhou et al. |
| 2009/0149952 A1 | 6/2009 | Shadduck |

(56) References Cited

U.S. PATENT DOCUMENTS

| | | |
|---|---|---|
| 2009/0171366 A1 | 7/2009 | Tanaka |
| 2009/0204123 A1 | 8/2009 | Downer |
| 2009/0228101 A1 | 9/2009 | Zadno-Azizi |
| 2009/0234366 A1 | 9/2009 | Tsai et al. |
| 2009/0234449 A1 | 9/2009 | De Juan, Jr. et al. |
| 2009/0248154 A1 | 10/2009 | Dell |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0318933 A1 | 12/2009 | Anderson |
| 2009/0319040 A1 | 12/2009 | Khoury |
| 2010/0016963 A1 | 1/2010 | Park |
| 2010/0039709 A1 | 2/2010 | Lo |
| 2010/0063588 A1 | 3/2010 | Park |
| 2010/0094412 A1 | 4/2010 | Wensrich |
| 2010/0131058 A1 | 5/2010 | Shadduck |
| 2010/0161049 A1 | 6/2010 | Inoue |
| 2010/0179653 A1 | 7/2010 | Argento et al. |
| 2010/0204705 A1 | 8/2010 | Brown et al. |
| 2010/0228344 A1 | 9/2010 | Shadduck |
| 2010/0228346 A1 | 9/2010 | Esch |
| 2010/0324671 A1 | 12/2010 | Shadduck |
| 2011/0118834 A1 | 5/2011 | Lo et al. |
| 2011/0153015 A1 | 6/2011 | Simonov et al. |
| 2011/0208301 A1 | 8/2011 | Anvar et al. |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2012/0022547 A1 | 1/2012 | Hildebrand et al. |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0226351 A1 | 9/2012 | Peyman |
| 2012/0245591 A1 | 9/2012 | Matthews |
| 2012/0253458 A1 | 10/2012 | Geraghty et al. |
| 2012/0253459 A1 | 10/2012 | Reich et al. |
| 2013/0053954 A1 | 2/2013 | Rao et al. |
| 2013/0060331 A1 | 3/2013 | Shadduck |
| 2013/0103146 A1 | 4/2013 | Smiley et al. |
| 2013/0131794 A1 | 5/2013 | Smiley et al. |
| 2013/0250239 A1 | 9/2013 | Hildebrand et al. |
| 2013/0268070 A1 | 10/2013 | Esch et al. |
| 2014/0121768 A1 | 5/2014 | Simpson |
| 2014/0142588 A1 | 5/2014 | Hildebrand et al. |

FOREIGN PATENT DOCUMENTS

| | | |
|---|---|---|
| EP | 1356791 B1 | 4/2006 |
| EP | 1332731 B1 | 8/2007 |
| EP | 1659991 B1 | 5/2009 |
| EP | 2060243 A1 | 5/2009 |
| EP | 2346441 B1 | 3/2013 |
| FR | 2784575 | 4/2000 |
| JP | 07-044938 | 5/1995 |
| JP | 8501715 | 2/1996 |
| JP | 8224295 | 9/1996 |
| JP | 9294754 | 11/1997 |
| JP | 10-206609 | 8/1998 |
| JP | 11-47168 A | 2/1999 |
| JP | 11056998 | 3/1999 |
| JP | 11276509 | 10/1999 |
| JP | 2001-502592 A | 2/2001 |
| JP | 2003144387 | 5/2003 |
| JP | 2003-524503 A | 8/2003 |
| JP | 2003530978 | 10/2003 |
| JP | 2006341094 | 12/2006 |
| JP | 2007513715 A | 5/2007 |
| JP | 2007518447 A | 7/2007 |
| JP | 2008-534111 A | 8/2008 |
| JP | 2008531069 | 8/2008 |
| JP | 2008307394 A | 12/2008 |
| JP | 200934451 | 2/2009 |
| SU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 A2 | 2/2004 |
| WO | WO 2004/046768 A2 | 6/2004 |
| WO | WO 2004/072689 A2 | 8/2004 |
| WO | WO 2005/018504 A1 | 3/2005 |
| WO | WO 2005/084588 A1 | 9/2005 |
| WO | WO 2006/004707 A2 | 1/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007005692 A1 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO 2007/138564 A1 | 12/2007 |
| WO | WO 2009/100322 A2 | 8/2009 |
| WO | WO 2009/154455 A1 | 12/2009 |
| WO | WO 2011/119334 A1 | 9/2011 |
| WO | WO 2012/006186 A2 | 1/2012 |
| WO | WO 2012/129419 A1 | 9/2012 |

OTHER PUBLICATIONS

Baughman, "Avoiding the shrink," Nature, vol. 425, pp. 667, Oct. 16, 2003.

Conlisk, A. T. et al; Mass Transfer and Flow in Electrically Charged Micro- and Nano-channels; Analytical Chemistry, vol. 74; iss. 9; pp. 2139-2150; May 2002.

Dubbelman et al.; The Thickness of the Aging Human Lens Obtained from Corrected Scheimpflug Images; Optometry & Vison Science; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," Proceedings of the First Intl Conf. on Shape Memory and Superelastic Tech., Asilomar Conference Center, Pacific Grove, CA, USA, pp. 115-120, Mar. 1994.

Gruber et al.; Exhaustive soxhlet extraction for the complete removal of residual compounds . . . ; Journal of Biomedical Materials Research; vol. 53; No. 5; pp. 445-448; Mar. 2000.

Jeon et al., "Shape memory and nanostructure in poly(norbornyl-POSS) copolymers," Polymer International, vol. 49, pp. 453-457, May 2000.

Kim et al., "Polyurethanes having shape memory effects," Polymer, vol. 37, No. 26, pp. 5781-5793, Dec. 1996.

Lakes et al., "Dramatically stiffer elastic composite materials due to negative stiffness phase?," Journal of the Mechanics and Physics of Solids, vol. 50, pp. 979-1009, May 2002.

Lakes et al., "Extreme damping in composite materials with negative-stiffness inclusions," Nature, vol. 410, pp. 565-567, Mar. 29, 2001.

Lakes et al., "Microbuckling instability in elastomeric cellular solids," J. Materials Science, vol. 28, pp. 4667-4672, Jan. 1993.

Lakes, "A broader view of membranes," Nature, vol. 414, pp. 503-504, Nov. 29, 2001.

Lakes; Deformations in extreme matter; Science; perspectives; vol. 288; No. 5473; pp. 1976-1977; Jun. 16, 2000.

Lakes, "Extreme damping in compliant composites with a negative-stiffness phase," Philosophical Magazine Letters, vol. 81, No. 2, pp. 95-100, Feb. 2001.

Lakes, "Extreme damping in composite materials with a negative stiffness phase," Physical Review Letters, vol. 86, No. 13, pp. 2897-2900, Mar. 26, 2001.

Lakes, "Negative poisson's ratio materials," Science, vol. 238, pp. 551, Oct. 23, 1987.

Lakes, "No contractile obligations," Nature, vol. 358, pp. 713-714, Dec. 31, 1992.

(56) References Cited

OTHER PUBLICATIONS

Langenbucher et al., "Computerized calculation scheme for toric intraocular lenses," Acta Ophthalmologica Scandinavica, vol. 82, No. 3, pp. 270-276, Jun. 2004.

Lendlein et al., "Biodegradable, elastic shape-memory polymers for potential biomedical applications", Science; vol. 296; pp. 1673-1676; May 31, 2002.

Lendlein et al., "Shape-memory polymers," Angew. Chem. Int. Ed.; vol. 41; pp. 2034-2057; Jun. 2002.

Li et al., "Crystallinity and morphology of segmented polyurethanes with different soft-segment length," Journal of Applied Polymer Science, vol. 62, pp. 631-638, Oct. 1996.

Liu et al., "Thermomechanical characterization of a tailored series of shape memory polymers," Journal of Applied Medical Polymers, vol. 6, No. 2, Dec. 2002.

Mather et al., "Strain recovery in POSS hybrid thermoplastics," Polymer Preprints, vol. 41, No. 1, pp. 528-529, Feb. 2000.

Metcalfe et al., "Cold hibernated elastic memory foams for endovascular interventions," Biomaterials, vol. 24, pp. 491-497, Feb. 2003.

Qiao et al.; Bio-inspired accommodating fluidic intraocular lens; Optics Letters; vol. 34; No. 20; pp. 3214-3216; Oct. 15, 2009.

Rosales et al.; Pentacam Scheimpflug QuantitativeImaging of the Crystalline Lens andIntraocular Lens; J. Refractive Surgery; vol. 25; pp. 421-428; May 2009.

Takahashi et al., "Structure and properties of shape-memory polyurethane block copolymers," Journal of Applied Polymer Science, vol. 60, pp. 1061-1069, May 1996.

Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.

Tobushi et al., "Thermomechanical properties of shape memory polymers of polyurethane series and their applications," Journal de Physique IV, Colloque C1, vol. 6, pp. 377-384, Aug. 1996.

Vass et al.; Prediction of pseudophakic capsular bag diameter based on biometric variables; J Cataract Refract Surg.; vol. 25; pp. 1376-1381; Oct. 1999.

Wang et al., "Deformation of extreme viscoelastic metals and composites," Materials Science and Enginerring A, vol. 370, pp. 41-49, Apr. 2004.

Wang et al., "Extreme stiffness systems due to negative stiffness elements," American Journal of Physics, vol. 72, No. 1, pp. 40-50, Jan. 2004.

Wang et al., "Stable extremely-high-damping discrete viscoelastic systems due to native stiffness elements," Applied Physics Letters, vol. 84, No. 22, pp. 4451-4453, May 31, 2004.

Wyant et al; "Basic Wavefront Aberration Theory for Optical Metrology," Applied Optics and Optical Engineering, vol. XI, Aug. 10, 1992: pp. 1, 28-39.

Xu et al., "Making negative poisson's ratio microstructures by soft lithography," Advanced Materials, vol. 11, No. 14, pp. 1186-1189, Jun. 1999.

Shadduck, John; U.S. Appl. No. 14/278,249 entitled "Accommodating intraocular lens," filed May 15, 2014.

\* cited by examiner

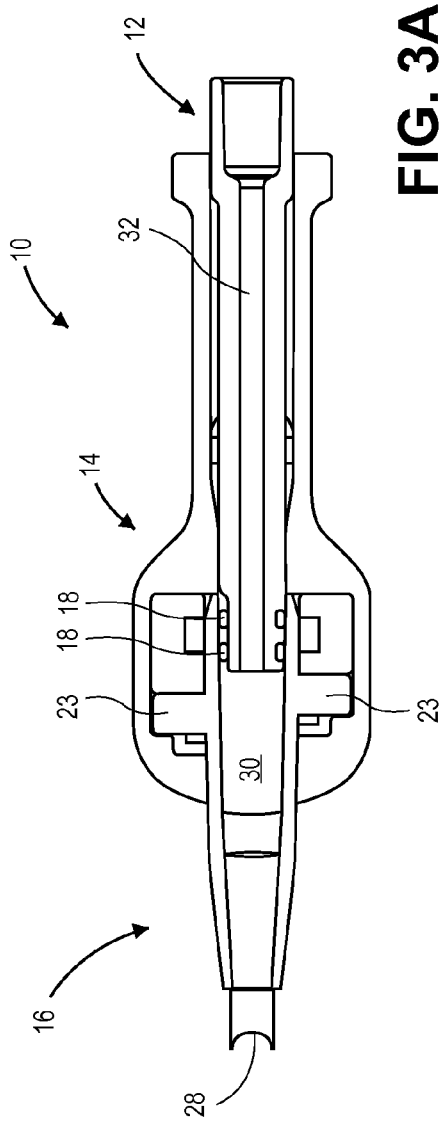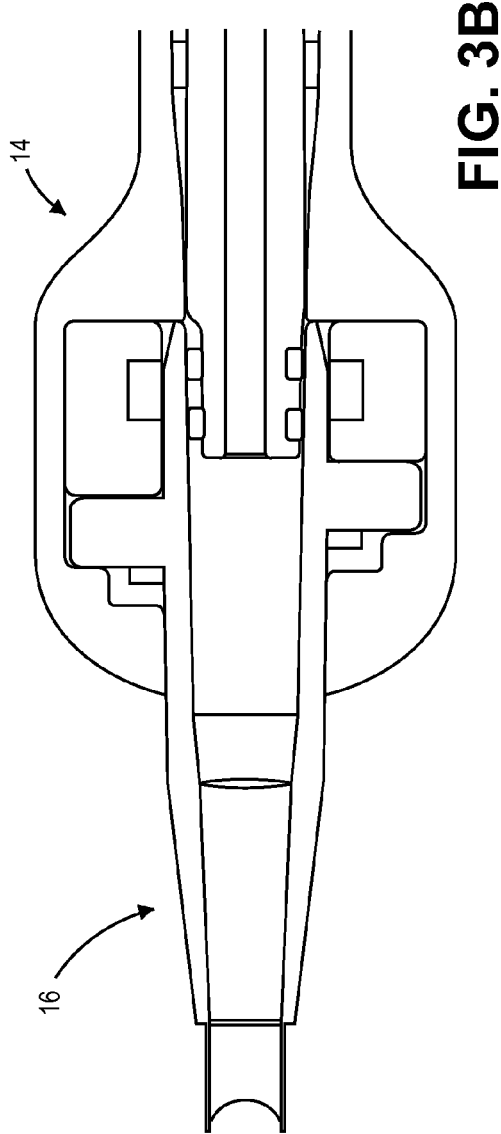

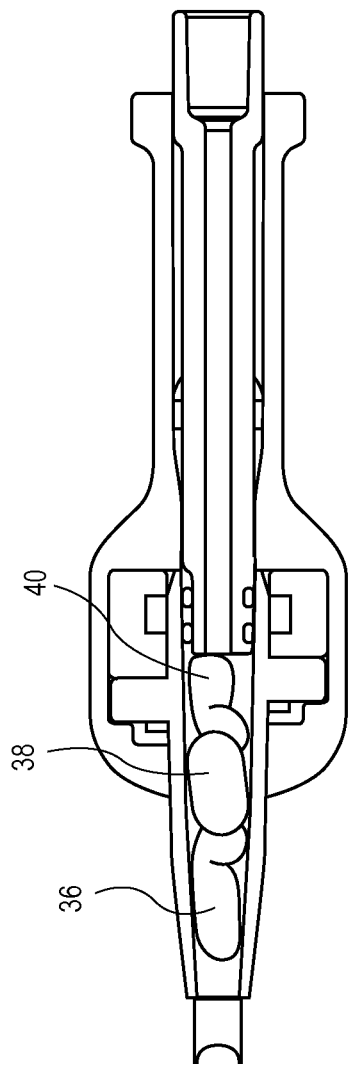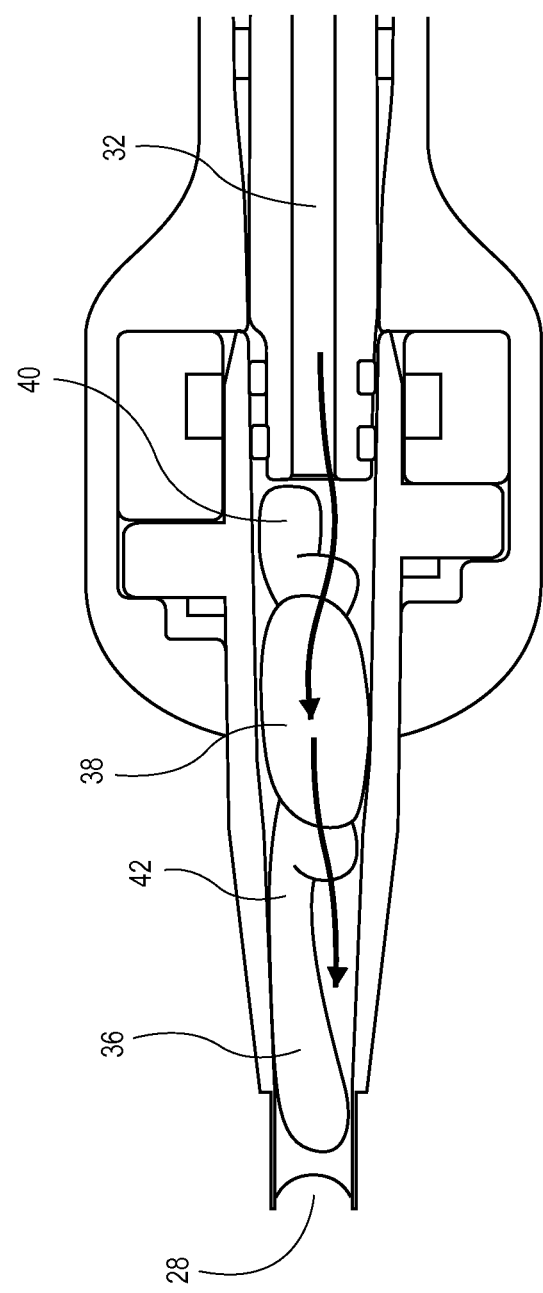

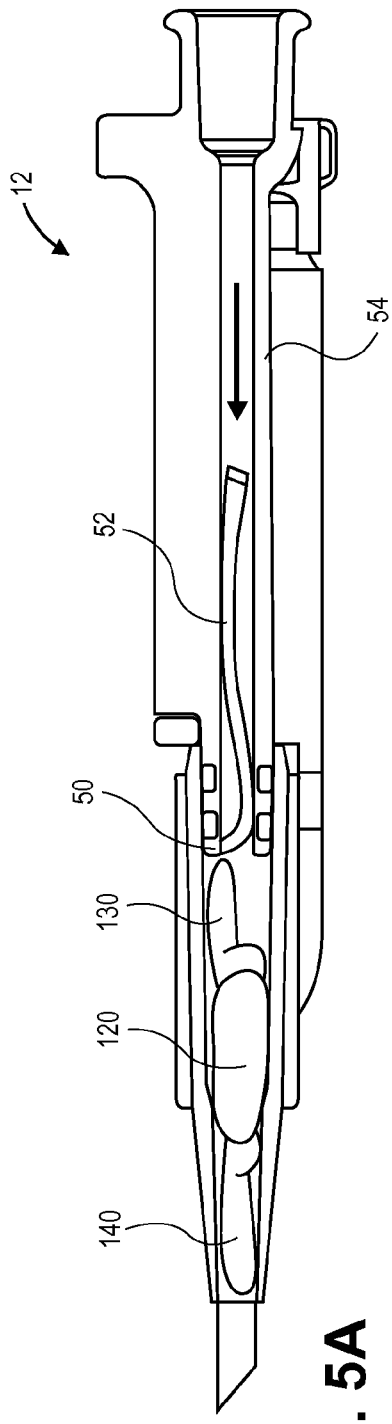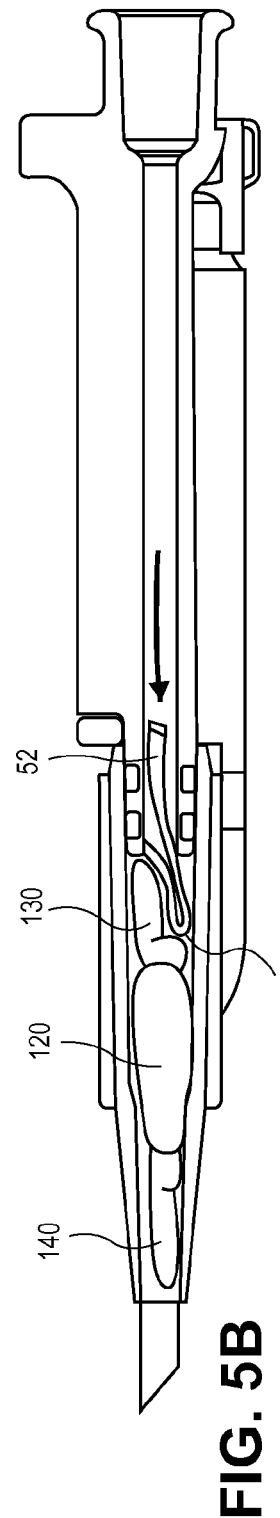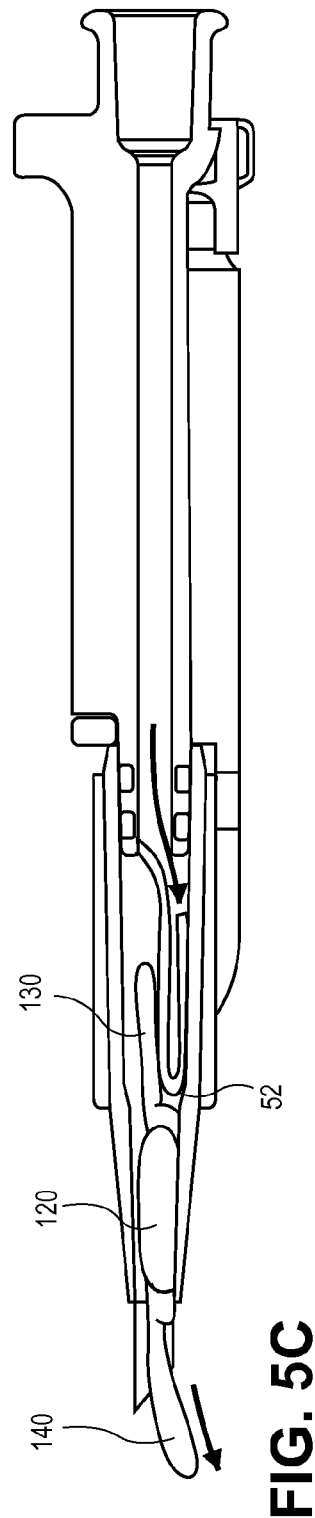

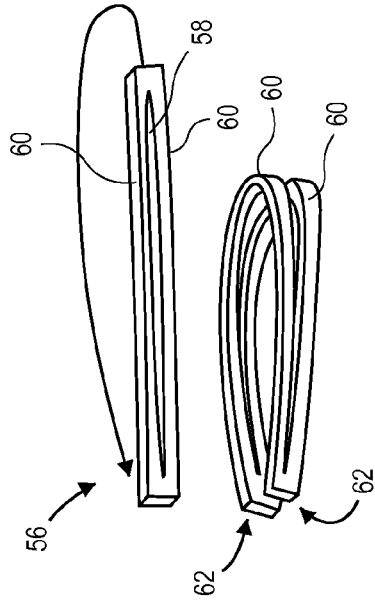
FIG. 6A
FIG. 6B
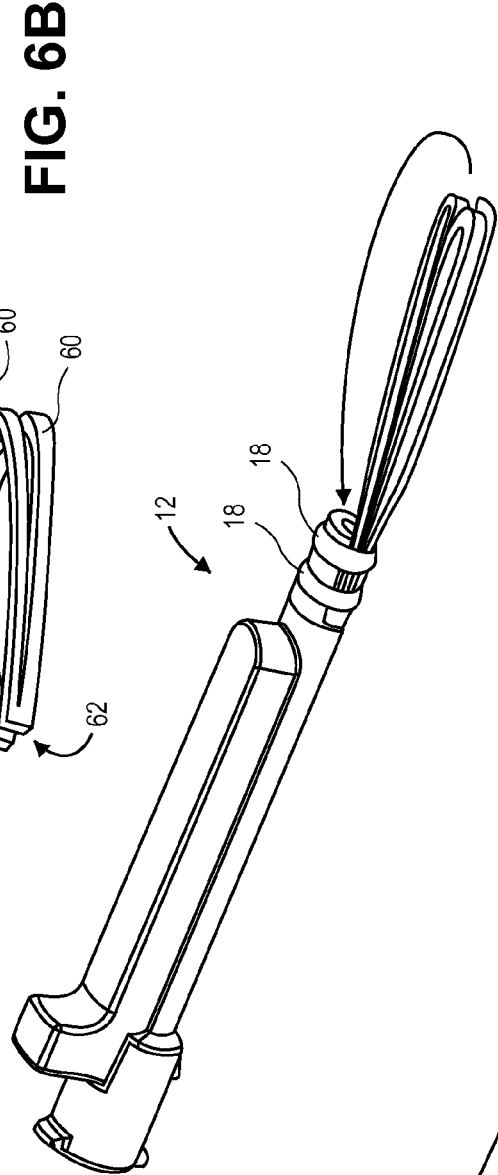
FIG. 7A
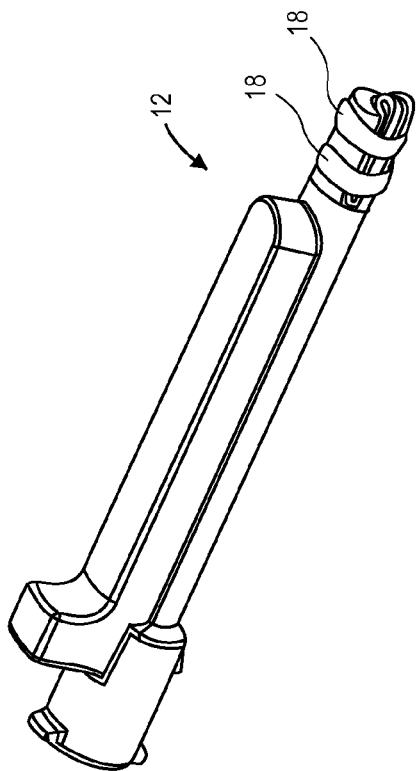
FIG. 7B

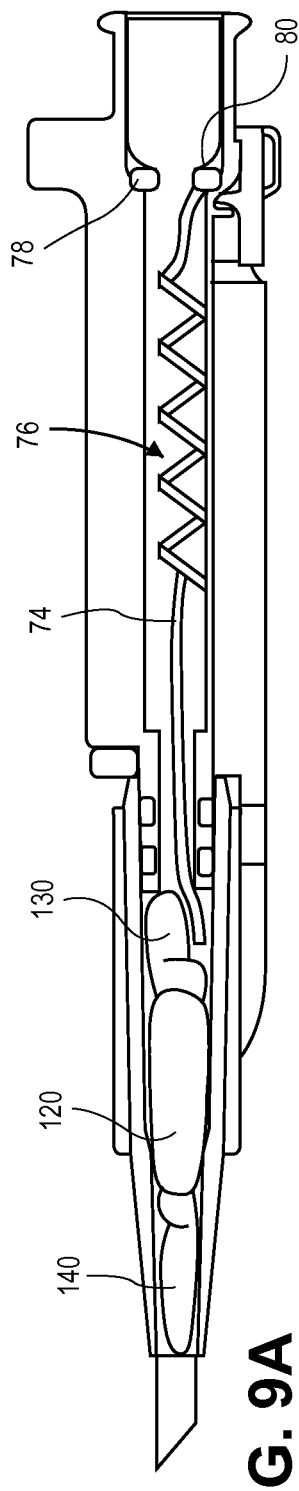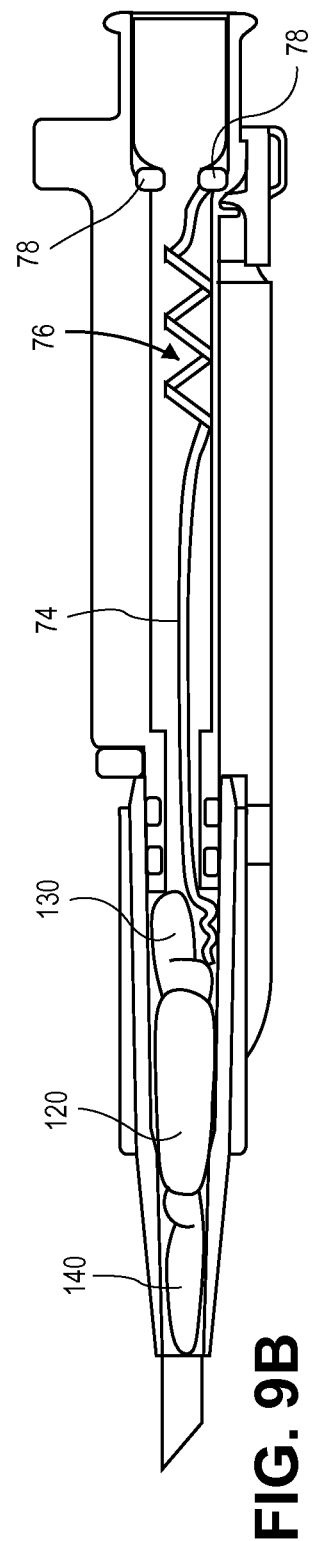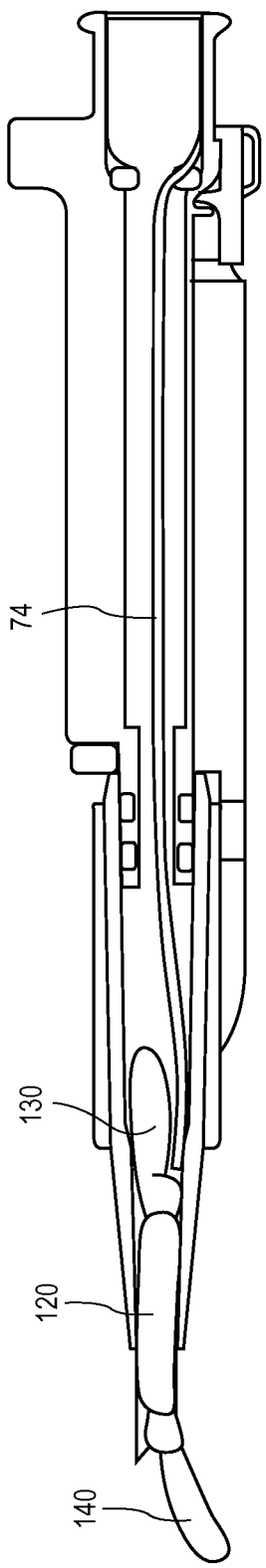

INTRAOCULAR LENS DELIVERY SYSTEMS AND METHODS OF USE

CROSS REFERENCE TO RELATED APPLICATIONS

This application is a continuation-in-part application of U.S. application Ser. No. 12/178,565, filed Jul. 23, 2008, which claims priority to U.S. Prov. App. No. 60/951,439, filed Jul. 23, 2007, the disclosures of which are incorporated by reference herein.

This application also claims the benefit of U.S. Prov. App. No. 61/613,929, filed Mar. 21, 2012, the disclosure of which is incorporated by reference herein.

This application is related to and incorporates by reference herein the disclosures of the following U.S. patent applications: U.S. application Ser. No. 13/180,427, filed Jul. 11, 2011, and U.S. application Ser. No. 13/427,617, filed Mar. 22, 2012.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Intraocular lenses are positioned within a patient's eye, such as in the anterior chamber or posterior chamber. After making a small incision in the eye, a physician typically positions a distal opening of a delivery device within or adjacent to the opening. The physician then delivers the intraocular lens out of the delivery device, through the opening, and into the target location within the eye. In some procedures, but not all, an intraocular lens is delivered into a native capsule after the native lens has been removed.

Some intraocular lenses, because of their size and/or their configuration, and possibly the desired incision size, need to be reconfigured and/or have at least a first portion reoriented with respect to a second portion to be delivered into an eye. When some intraocular lenses are advanced through a delivery device and/or delivered out of the delivery device, forces on the intraocular lens can damage the intraocular lens.

What are needed are delivery systems and methods of use that can deliver an intraocular lens without damaging the intraocular lens.

SUMMARY OF THE DISCLOSURE

One aspect of the disclosure is a method of deploying an intraocular lens into an eye, comprising providing an intraocular lens within a delivery device; at least partially plugging a gap between the intraocular lens and an inner surface of the delivery device; and delivering a fluid into the delivery device to deploy the intraocular lens from the delivery device and into an eye. In some embodiments at least partially plugging a gap reduces the amount of fluid that flows past the intraocular lens in the delivery device. In some embodiments at least partially plugging a gap allow for an increase in fluid pressure in the delivery device proximal to an optic portion of the intraocular lens. In some embodiments at least partially plugging a gap increase a pressure differential in the delivery device between a location proximal to an optic portion of the intraocular lens and a location distal to the intraocular lens. In some embodiments at least partially plugging a gap comprises at least partially plugging a gap that is disposed radially between the intraocular lens and an inner surface of the delivery device. In some embodiments at least partially plugging a gap between the intraocular lens and an inner surface of the delivery device comprises at least plugging a gap that exists between a trailing haptic and an inner surface of the delivery device. In some embodiments the method further comprises reconfiguring a plugging element while delivering the fluid into the delivery device. Reconfiguring the plugging element can act to form a seal between the plugging element and an inner surface of the delivery device. Reconfiguring the plugging element can include unrolling the plugging element.

In some embodiments delivering a fluid into the delivery device to deploy the intraocular lens from the delivery device comprises delivering a fluid through a porous material.

One aspect of the disclosure is a method of deploying an intraocular lens into an eye, comprising providing an intraocular lens within a delivery device; at least partially plugging a gap disposed radially between the intraocular lens and an inner surface of the delivery device; and delivering a fluid into the delivery device to deploy the intraocular lens from the delivery device. In some embodiments at least partially plugging a gap disposed radially between the intraocular lens and an inner surface of the delivery device comprises at least partially plugging a gap disposed radially between a haptic extending generally longitudinally through the delivery device and in inner surface of the delivery device.

One aspect of the disclosure is a method of deploying an intraocular lens into an eye, comprising providing an intraocular lens within a delivery device; delivering a fluid into the delivery device to deploy the intraocular lens from the delivery device; and increasing fluid pressure proximal to at least an optic portion of the IOL, wherein increasing the fluid pressure is a step different than delivering the fluid into the delivery device. In some embodiments increasing fluid pressure proximal to at least an optic portion of the IOL comprises plugging a gap between the IOL and an inner surface of the delivery device.

One aspect of the disclosure is an apparatus for deploying an intraocular lens into an eye, comprising: an intraocular lens delivery device with an intraocular lens disposed therein; a support device adapted to be disposed within the delivery device, the support device having a lumen therein adapted to allow to fluid to flow therethrough; and a plug element disposed relative to the support device such that it is adapted to at least partially plug a gap between an intraocular lens positioned in the delivery device and an inner surface of the delivery device.

In some embodiments the support device is secured to the plug element. The plug element can have a proximal portion secured to the support device. In some embodiments the plug element is a tubular element. In some embodiments the plug element is open at a distal end after deployment. In some embodiments the plug element has a fluid flow restriction proximal to a distal end of the plug element. In some embodiments the plug element is everted at a distal end. In some embodiments the plug element is flexible. In some embodiments the plug element is porous. In some embodiments the plug element is adapted to be reconfigured in response to fluid flow through the lumen. Only a distal portion of the plug element can be adapted to be reconfigured. In some embodiments the plug element has a flow restriction proximal to a distal end of the plug element. The plug element can have a portion distal to the flow restriction that is adapted to be reconfigured.

In some embodiments the plug element is open at a distal end. In some embodiments the plug element is an ePTEF tube. In some embodiments a distal portion of the support element is oriented towards an inner wall of the delivery device. In some embodiments a distal portion of the support element is oriented away from a longitudinal axis of a proximal portion of the support element. In some embodiments a trailing haptic extends proximal relative to an optic portion of the intraocular lens. The plug element can be disposed radially between the intraocular lens and an inner surface of the delivery device. In some embodiments the apparatus further comprises a vent adapted to vent air from inside the apparatus.

One aspect of the disclosure is an apparatus for deploying an intraocular lens into an eye, comprising: an intraocular lens delivery device and an intraocular lens disposed therein; an support device adapted to be disposed within the delivery device, the support device having a lumen therein adapted to allow to fluid to flow therethrough; and a flexible plug element secured to the support device, the plug element adapted to at least partially plug a gap between an intraocular lens positioned in the delivery device and an inner surface of the delivery device when fluid is flowed into the lumen.

One aspect of the disclosure is an apparatus for deploying an intraocular lens into an eye, comprising: an intraocular lens delivery device with an intraocular lens disposed therein; a support device adapted to be disposed within the delivery device, the support device having a lumen therein adapted to allow to fluid to flow therethrough; and a vent that is not an intraocular lens delivery port, the vent adapted to vent air from inside the delivery device when fluid flows therethrough.

One aspect of the disclosure is a method of deploying an intraocular lens into an eye, comprising providing an intraocular lens within a delivery device; delivering a fluid into the delivery device to deploy the intraocular lens from the delivery device; and venting air from within the delivery device through a vent, wherein the vent is not an intraocular lens delivery port.

BRIEF DESCRIPTION OF THE DRAWINGS

FIGS. 3A and 3B illustrate a portion of an exemplary intraocular lens delivery device.

FIGS. 4A and 4B illustrate an exemplary intraocular lens delivery device with an intraocular lens therein.

FIGS. 5A-5C illustrate an exemplary intraocular lens delivery device with a sealing element.

FIGS. 6A and 6B illustrate an exemplary sealing element.

FIGS. 7A and 7B illustrate an exemplary intraocular lens delivery device with a sealing element deployed and loaded.

FIGS. 9A-9C illustrate an exemplary intraocular lens delivery device with a sealing, or plugging, element delivering an intraocular lens from a distal delivery port.

DETAILED DESCRIPTION

The disclosure is related to methods and devices for delivering an intraocular lens ("IOL") into an eye. The systems and methods herein can, however, be used to advance any type of IOL within a delivery or loading device. The intraocular lens can be accommodating or non-accomodating. The methods and devices herein may be beneficial when the IOL body does not occupy the entire volume of a section of the delivery device in which the IOL is positioned.

An IOL is typically implanted within a patient's eye to replace or supplement the function of an eye's native lens. The native lens can become diseased (e.g., cataract), or the lens can lose the ability to accommodate over time (i.e., presbyopia). In either case, the native lens can be removed and replaced with an IOL. To deliver the IOL through as small an incision as reasonable (e.g., about 2.8 mm to about 4.5 mm), the IOL typically undergoes some type of deformation or reconfiguration during the loading and/or delivery process to reduce the profile of the IOL. Additionally, some IOLs include components that can be reoriented and/or reconfigured relative to another component, such as a peripheral portion relative to an optic portion, and the controlled positioning or deformation of these components during the loading and/ or delivery steps can enhance the loading and/or delivery and reduce the likelihood of damage to the IOL.

In some embodiments the delivery systems can be used to deliver an IOL that have one or more flowable media therein. For example, the delivery systems can be used to deliver fluid-filled accommodating IOLs, while in some embodiments the IOL may comprise a low viscosity polymeric material. The disclosure is not limited by the exemplary IOLs provided herein. Any suitable IOL that can benefit from the use of the systems and methods of herein can be delivered as described herein.

Figure 1:
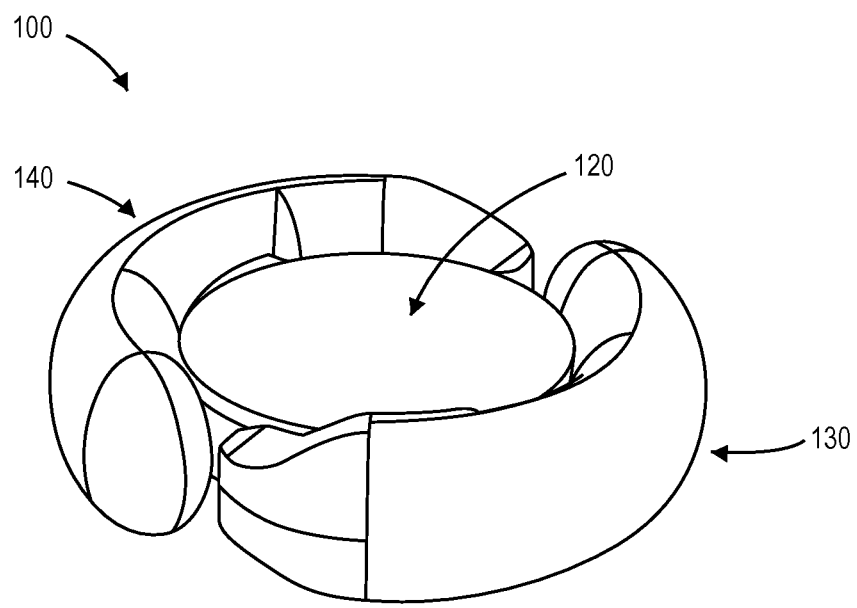
FIG. 1 illustrates an exemplary accommodating intraocular lens that can be delivered into an eye using any of the delivery devices herein.

FIG. 1 illustrates an exemplary intraocular lens that is delivered in any of the method herein. Accommodating intraocular lens 100 includes optic body 120 with a fluid chamber therein that is in fluid communication with fluid chambers in haptic 130 and haptic 140. Haptics 130 and 140, part of the peripheral portion of the IOL, are responsive to capsular reshaping, and the IOL is adapted such that flowable media, such as a fluid, is moved between the haptics and optic in response to capsular reshaping. Additional exemplary details of accommodating IOL 100 can be found in U.S. application Ser. No. 13/672,608, filed Nov. 8, 2012, which is incorporated by reference herein.

Figure 2A:
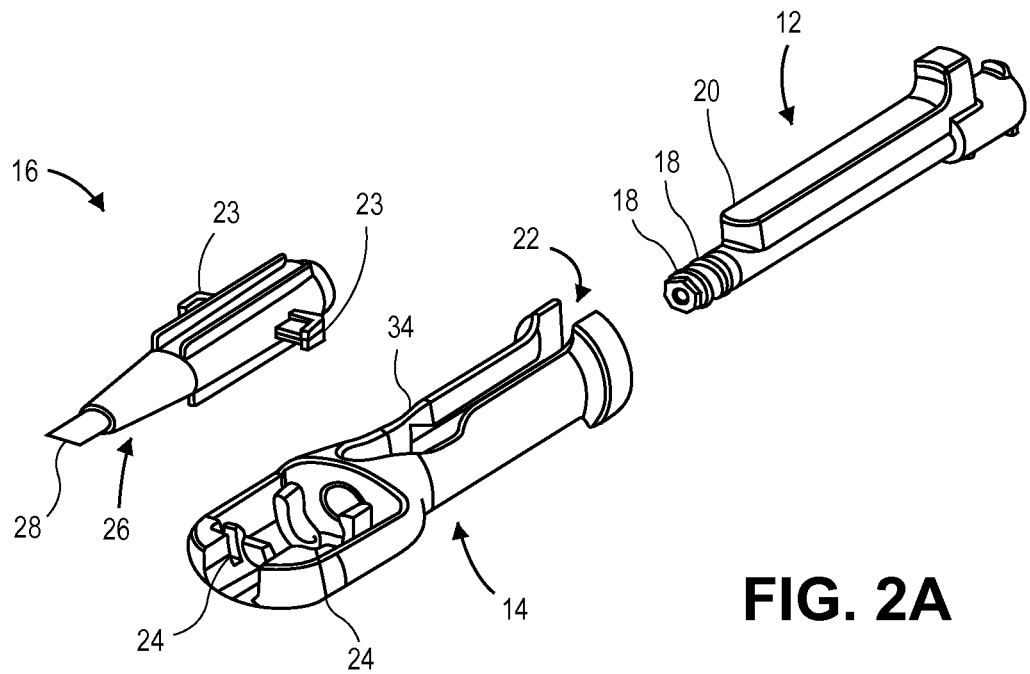
FIGS. 2A and 2B illustrate exploded and assembly views, respectively, of an exemplary intraocular lens delivery device.
Figure 2B:
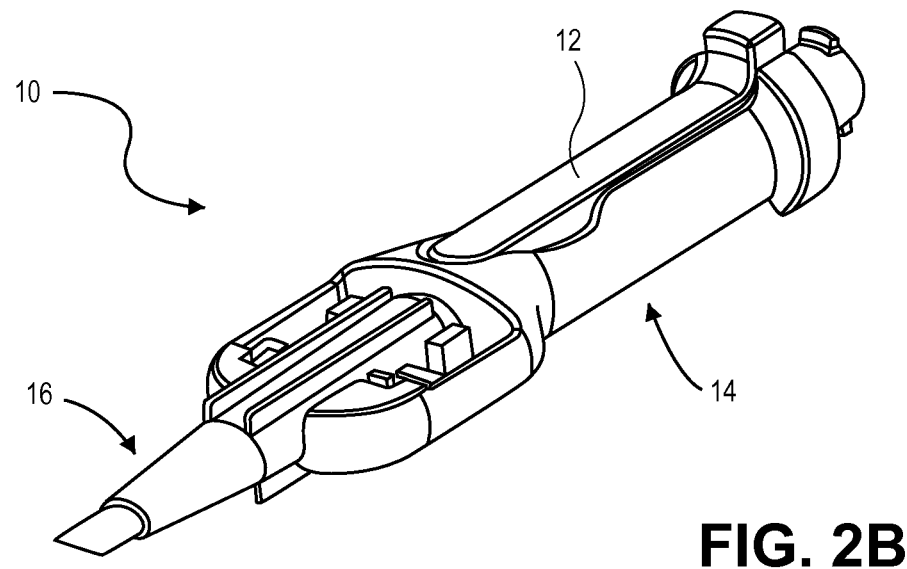

One first aspect of the disclosure is a delivery device adapted to deliver an accommodating intraocular lens, such as the intraocular lens shown in FIG. 1, into the eye. While the delivery device is described as delivering the lens shown in FIG. 1, it is understood that any other suitable lens can be delivered using the devices, systems, and methods described herein. FIGS. 2A and 2B illustrate an exploded view and assembly view, respectively, of an exemplary delivery device ("device" may be used interchangeably with "system" herein unless there is a specific indication to the contrary). FIGS. 3A and 3B illustrate top sectional views of the assembly, with FIG. 3B showing a partial sectional view of a distal portion of the assembly (only a portion of tray 14 and plunger 12 are shown). Delivery device 10 includes plunger 12, tray 14, and cartridge 16. Tray 14 is adapted to interact with plunger 12 and cartridge 16, allowing an intraocular lens to be delivered from within cartridge 16 into an eye. Tray 14 includes plunger guide 22 extending through a proximal portion that is adapted to receive plunger 12 therein (see FIG. 3A). Plunger 12 includes stop 20 that is configured to engage a complimentary stop feature on the tray to prevent further distal movement of plunger 12 within tray 14. Plunger 12 includes lumen 32 extending from its proximal end to its distal end, allowing material, such as viscoelastic fluid, to be advanced from the proximal end of plunger into the cartridge. Plunger 12 also includes sealing members 18 in the form of O-rings that engage with an inner surface of cartridge 16 and provide a fluid seal between the distal end of plunger 12, cartridge 16, and tray 14. Cartridge 16 includes stabilizing elements 23 that are adapted to secure the cartridge with respect to tray 14 by engaging corresponding stabilizing elements 24 on tray 14. As seen in FIGS. 3A and 3B, when plunger 12 is fully advanced within tray 14, and when cartridge 16 is interfacing tray 14, the distal end of plunger 12 is within the proximal end of channel extending through cartridge 16. This allows a material such as a viscoelastic fluid, or other material, to be delivered from the proximal end of the plunger into the cartridge, pushing the loaded intraocular lens (not shown) from within the cartridge out the distal tip 28 (shown with a bevel) and into the patient's eye. The tapering cartridge will previously have been placed through an incision in the eye allowing the lens to be delivered into the eye.

FIGS. 4A and 4B illustrate the exemplary intraocular lens from FIG. 1 already loaded into the cartridge lumen 30. The intraocular lens can be advanced from a staging area in the tray (referred to generally as 34 in FIG. 2A) into the cartridge by any suitable loading technique. In one approach, the intraocular lens is positioned within staging area 34 in a configuration such that leading haptic 36 is positioned generally distal to optic 38, while trailing haptic 40 is positioned generally proximal to optic 38. From this staged configuration, the lens can be advanced into cartridge. For example, the lens can be loaded into the cartridge with any suitable plunger by being pushed into the cartridge. The lens could also be hydraulically loaded into the cartridge using a fluid. The loading device and approach can vary and is not limited herein. In some embodiments the system includes a plunger that is both adapted to load the lens from the tray into the cartridge, and is also adapted to deliver the lens from the cartridge into the eye as described below. Additional exemplary loading devices can be found in U.S. Provisional Application No. 61/467,352, filed Mar. 24, 2011, the disclosure of which is incorporated by reference herein.

After the lens is loaded into the cartridge as shown in FIG. 4A, a viscoelastic fluid, or other type of fluid, is delivered from a syringe and into lumen 32 of plunger 12 (see FIG. 4B). The viscoelastic fluid is delivered from the distal port of plunger 12 and into contact with the intraocular lens, forcing the lens distally within cartridge and out the distal end 28 of the cartridge. In general, the delivery of the intraocular lens from the cartridge relies on development of pressure differential in the viscoelastic over the lens to move it down the reducing section of the cartridge (shown as surface 42 in FIG. 4B) and into the eye. The configuration of the lens in general and/or the configuration that the intraocular lens assumes when loaded into the proximal region of the cartridge, however, creates some gaps, which provide a path for some of the viscoelastic to leak past the optic portion, as shown by the flow arrows in FIG. 4B. Ideally, none (or substantially none) of the viscoelastic fluid flows past the optic body portion. Ideally, all or substantially all of the viscoelastic remains proximal to at least the optic body portion, building up pressure and forcing the lens to be deployed from the distal end of the cartridge. When the viscoelastic does flow past the lens body it can create drag on the leading haptic that is efficiently filling the tip of the cartridge (FIG. 4B). The advancing leading haptic can create a high strain at the connection between the haptic and the optic body, possibly causing damage at the connection point. Any intraocular lens that may be susceptible to damage while being delivered may benefit from the systems and methods described herein.

One approach to preventing the fluid from flowing past the optic body and reducing the risk of damage to the lens is to create an efficient seal behind the lens body to reduce the flow of viscoelastic around the lens body. In one specific embodiment the device includes a plunger that includes at least one component that creates a seal behind the lens body. The component preferably does not restrict the deployment of the trailing haptic from the cartridge during the last portion of the delivery process. Additionally, the component(s) preferably do not exit the distal end of the cartridge into the eye at the end of the delivery process. While the sealing component is described as part of the plunger herein, it is understood that the sealing component could be a part of the tray, the cartridge, or other part of the delivery device.

FIGS. 5A-5C (side views of the device shown in FIGS. 2A-4B) show a portion of a delivery sequence of the lens in which the delivery device includes a sealing component, or plug, in the form of a compliant filament of material that is introduced into the viscoelastic stream. The filament is adapted to flow toward and into the location at which the viscoelastic fluid is flowing past the lens body. Once impeded by a restriction, the filament collapses and further obstructs the fluid flow path. This develops a soft sealing mechanism behind the lens body that also follows the lens while moving for delivery. FIG. 5A illustrates the device including sealing component 52 in the form of a filament attached to the distal end of plunger 12 at attachment point 50. As shown in FIG. 5A, filament 52 is initially disposed within lumen 32 of plunger 12, with the filament distal end extending in the proximal direction within the lumen. As the viscoelastic fluid is advanced through lumen 32 from the proximal end of the plunger, as shown by the arrow in FIGS. 5A-C, filament 52 is carried by the fluid in the distal direction, as shown in FIG. 5B. The filament flows toward the location at which the viscoelastic fluid is flowing past the lens body and creates a seal, as shown in FIG. 5B. In FIG. 5B the filament is shown plugging up a space adjacent the trailing haptic 130, creating at least a substantial seal. Once the seal is formed, the force of the viscoelastic fluid on the lens body will properly cause both the leading haptic and the optic portion to be advanced distally within the cartridge. FIG. 5C shows the leading haptic partially deployed from the cartridge while the optic body has been properly advanced through the cartridge. As the fluid continues to be advanced through the plunger and into the cartridge, the lens is advanced further through the cartridge until the leading haptic 140, optic body 120, and trailing haptic 140 are delivered, in that order, from the cartridge and into the eye. Once delivered the lens will inherently revert toward its original configuration, which is generally shown in the sectional view of FIG. 1. The deployment occurs without damage to the lens, particularly at the attachment point between the leading haptic and the optic body.

FIGS. 6A and 6B illustrate an exemplary embodiment of filament 56 with slit 58 formed therein extending along substantially the entire length of filament 56. The slit forms two filament segments 60 extending along the length of filament 56. The length of the segments 60 is substantially greater than the width of the segments. Filament 56 from FIG. 6A is then folded to bring two ends 62 together, as shown in FIG. 6B. FIGS. 7A and 7B illustrate the folded filament attached to plunger 12. The filament is secured to the distal region of the plunger by compressing the two filament end regions under the two o-rings 18 that are a seal to the cartridge, as discussed above. To prepare the device for use, the segments 60, in the form of loops, are tucked within the plunger lumen and ready for deployment during the delivery, as shown in FIG. 7B. In use, the filament loops extend and roll out of the lumen in the viscoelastic stream and flow into an open volume behind the lens buttress and adjacent the trailing haptic as discussed above in the embodiment in FIGS. 5A-5C. The filament bunches into that area until sufficiently plugging the flow at which time the lens body moves forward. When the lens moves sufficiently forward to plug the tip completely and there is substantially no viscoelastic flow by the lens body, the filament will be left behind.

If, during the delivery, the optic body stops moving in the cartridge and the viscoelastic is leaking past the optic body again, the filaments are adapted to again move to the area of leakage to act as a plug to the viscoelastic and move the lens out of the cartridge. The filaments as described herein as therefore adapted to repeatedly, as may be necessary, find or seek out the region where fluid is flowing past the optic body, move to that location, and plug the leak.

The embodiment in FIGS. 5A-7B illustrate embodiments in which the proximal end of the filament is attached to the distal region and the exterior of the plunger, and the filament is considered to roll out of the plunger during delivery of the lens. This allows the filament to slide out of the plunger past the attachment location and the first contact with the lens will be with a region of the filament that is near the proximal end of the filament. The filament repositions into suitable plugging orientation. There are, however, a number of variations in attachment points of the filament to the plunger (or other portions of the delivery device) yielding variations in deployment of the filament.

Figure 8A:
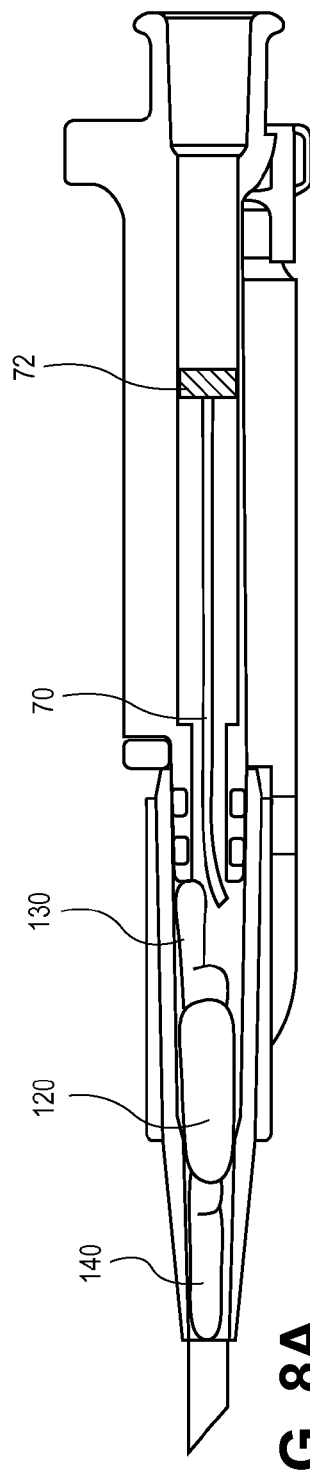
FIGS. 8A-8C illustrate an exemplary intraocular lens delivery device with a sealing, or plugging, element delivering an intraocular lens from a distal delivery port.
Figure 8B:
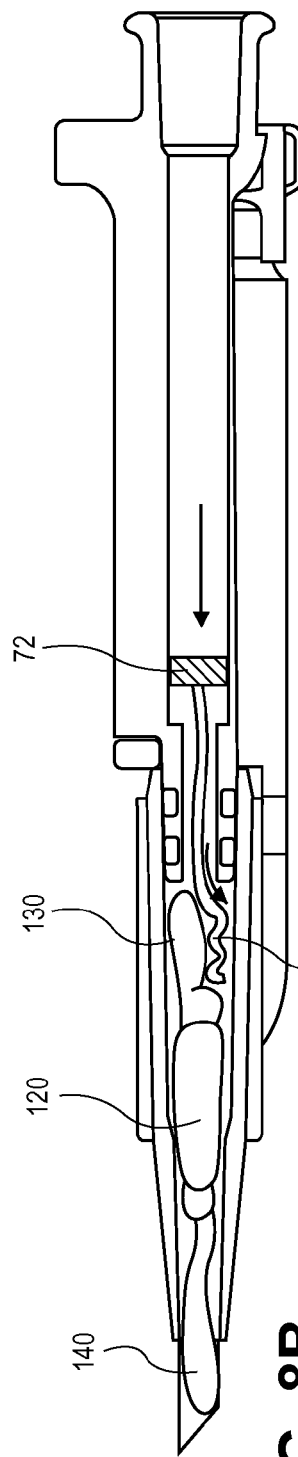
Figure 8C:
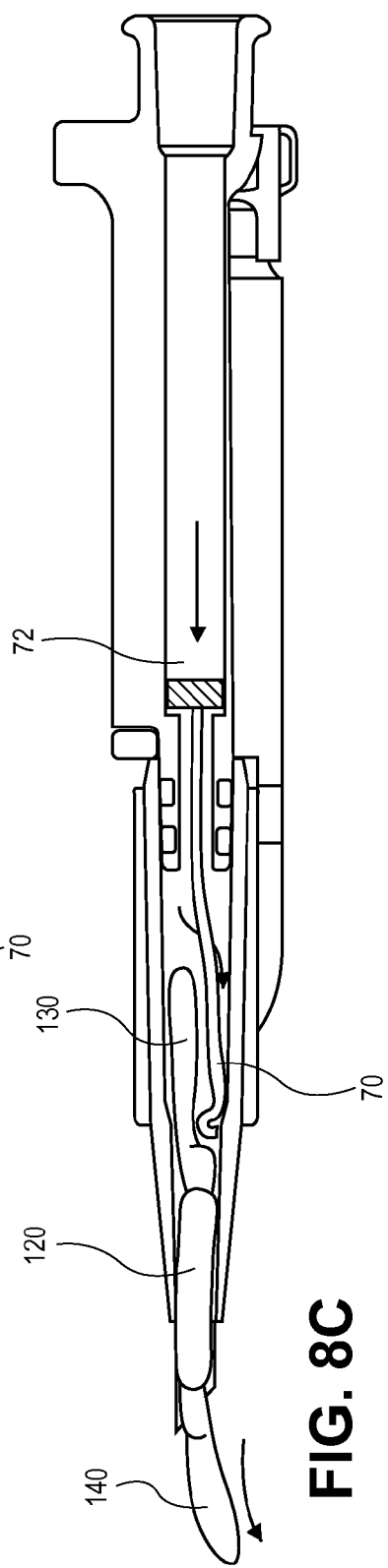

FIGS. 8A-8C illustrate an alternative embodiment in which the proximal end of the filament is attached to the distal region of the plunger, but is attached at a location on the interior of the plunger (i.e., within the plunger lumen). As indicated in FIG. 8A, the plunger has a proximal lumen section with a larger diameter bore than a distal tip section. Filament 70 is attached to stopper 72 at its proximal end. Filament 70 extends from stopper 70 towards the distal end of the plunger. The reduced diameter distal section acts as a lumen restriction and prevents stopper 72 from advancing further distally, as shown in FIG. 8C. This prevents the filament from flowing out of the distal tip of the cartridge. As the viscoelastic is delivered through the lumen, stopper 72 is advanced distally within the lumen, and filament 70 flows straight out of the lumen and does not double back (or fold) back on itself as in the previously described embodiments above. The filament is adapted to flow towards the flow leakage as described elsewhere herein.

Figure 15:
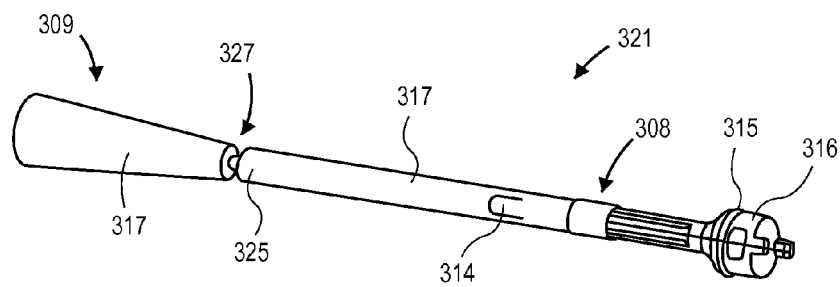
FIG. 15 illustrates an exemplary plugging element in a fully deployed configuration.

FIGS. 9A-9C illustrate sectional views of an alternative embodiment in which the proximal end of the filament 80 is secured to the proximal region of the plunger interior using press-ring filament capture 78, which is shown in greater detail in FIG. 15. Filament 74 includes a coiled or stretchable section 76 that is adapted to uncoil or stretch as the viscoelastic is delivered. The uncoiling or stretching of the filament effectively lengthens the filament, allowing the filament to be advanced into the cartridge to plug up any leaks, but is prevented from flowing out of the distal end of the cartridge. FIG. 9B shows the filament finding the leaking area and plugging it.

The embodiment shown in FIGS. 9A-9C includes a plunger with a distal tip region that has a reduced diameter relative to the proximal region. This feature can be incorporated into any the embodiments herein. The reduced diameter can create a relatively higher flow rate of fluid from the plunger distal tip, which helps pull the filament out of the distal end of the plunger. The increased flow rate minimizes tangles and compaction of the filament in the proximal end of the plunger as the viscoelastic is delivered.

Figure 10A:
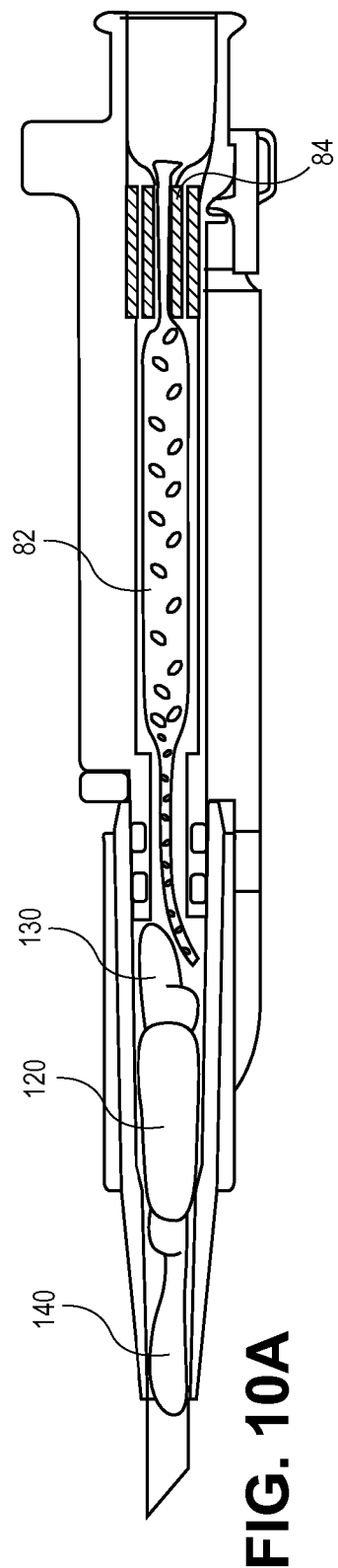
FIGS. 10A-10C illustrate an exemplary intraocular lens delivery device with a sealing, or plugging, element delivering an intraocular lens from a distal delivery port.
Figure 10B:
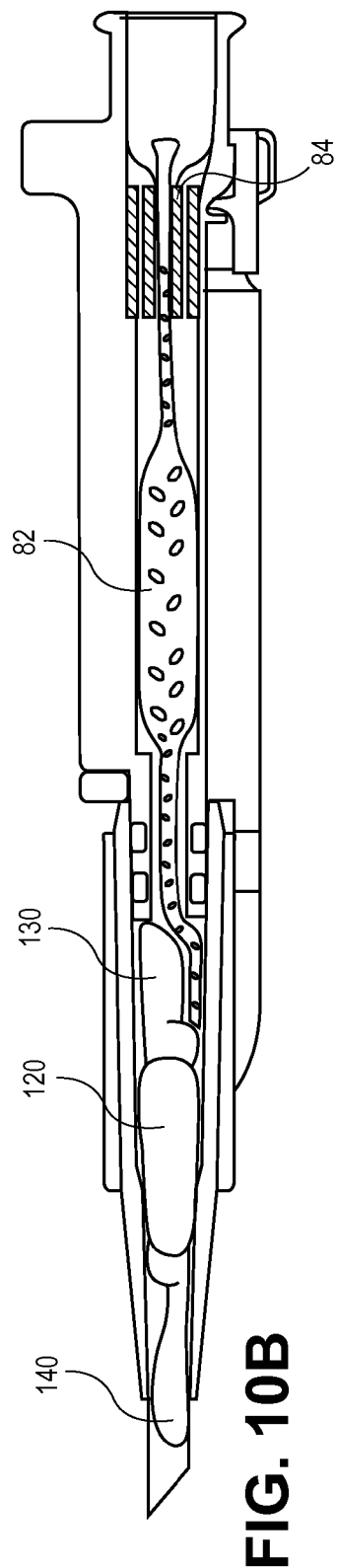
Figure 10C:
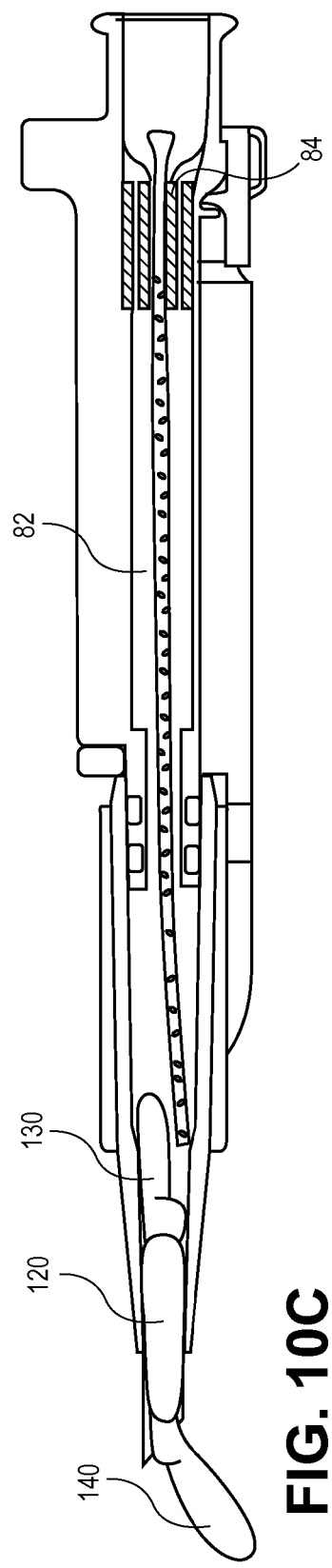
Figure 11A:
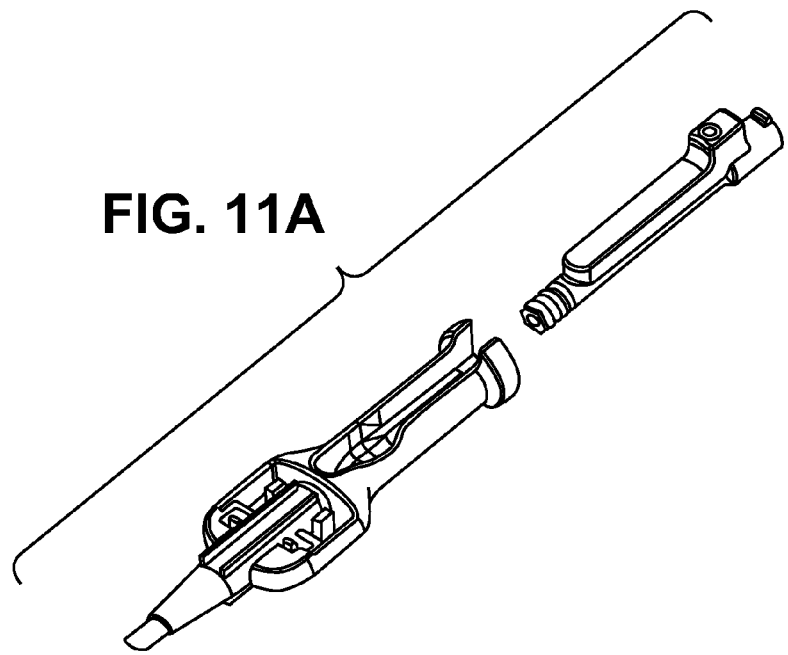
FIGS. 11A-11C illustrate an exemplary intraocular lens delivery device with a sealing, or plugging, element.
Figure 11B:
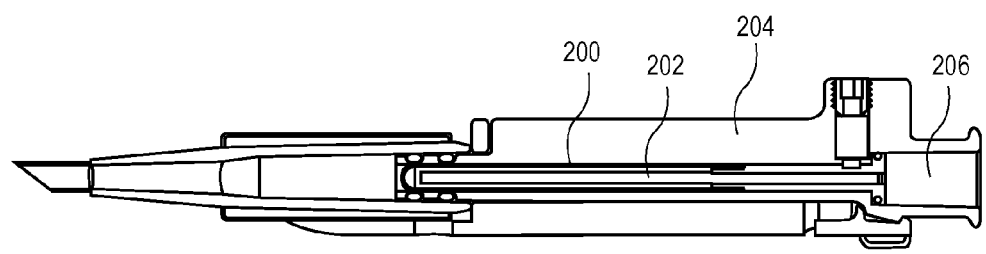
Figure 11C:
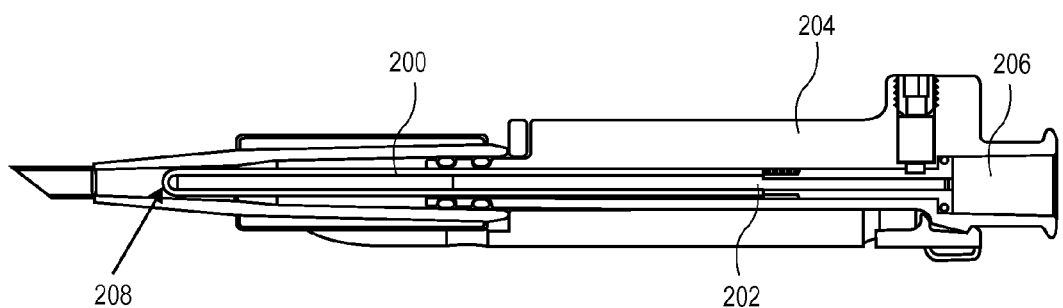
Figure 12A:
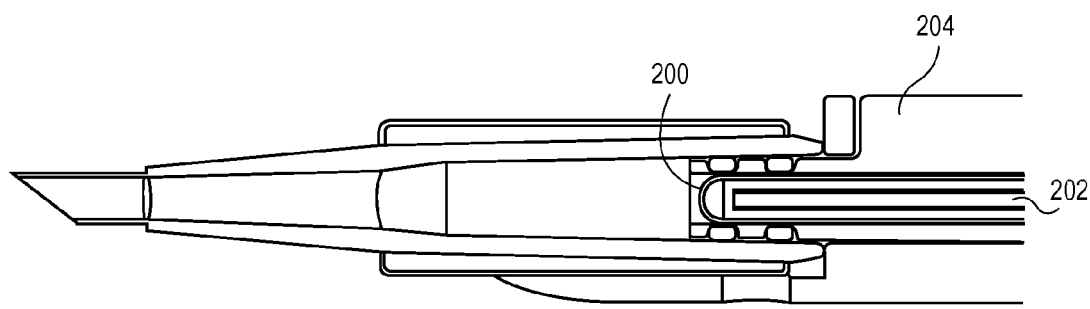
FIGS. 12A and 12B illustrate an exemplary intraocular lens delivery device with a sealing, or plugging, element.
Figure 12B:
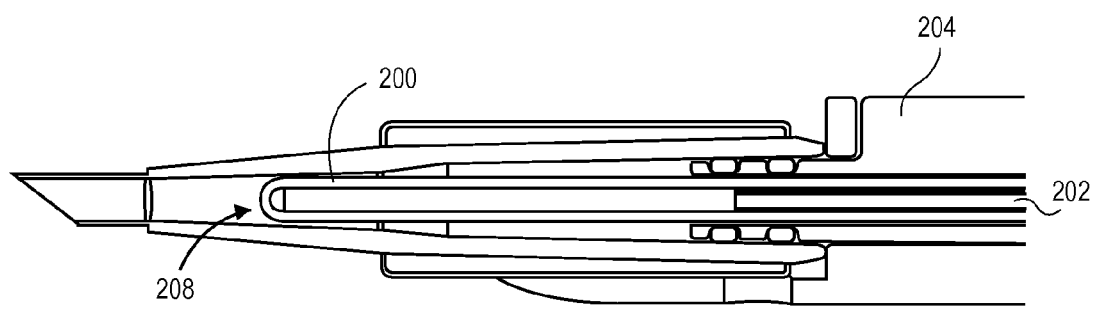

FIGS. 10A-10C illustrate an alternative embodiment similar to that in FIGS. 9A-9C in that the proximal end of the filament 82 is attached to an internal proximal region of the plunger 84. In this embodiment the filament 82 is a material that has a stretching property to it, such as a material that is perforated in such a way that it compresses efficiently in the plunger lumen (see FIG. 10A) and yet stretches to a static length when deployed (see FIG. 10C). In this embodiment the filament is an axially compressed perforated tubing. The filament is secured at its proximal end 845, and the plunger has a fluid channel radially outward from the attachment point. This is shown in FIG. 10B, in which the fluid flow is indicated the arrows. The fluid causes the perforated tubing to stretch as shown in FIG. 10B. This plunger design, with the distal reduced diameter, provides for a low velocity flow region and a high velocity flow region in the distal region. FIG. 10B illustrates the plunger sealing the leak, and FIG. 10C illustrates the leading haptic being deployed from the cartridge.

The filament material and design should be selected to enable the filament to seal the fluid flow as described above. An optimization of material structure and properties will generally provide a filament that is best suited to seal the fluid flow and allow for the intraocular lens to be delivered undamaged. It is envisioned, however, that in some instances it may be desirable to have some amount of fluid that does pass the optic body, after which the sealing should occur. The filament material can theoretically be selected that will provide that functionality to the system.

The properties of the filament will influence how it responds during the delivery process. Properties that can be modified to accomplish the specific goal include without limitation, compliance, coefficient of friction, and elasticity. In embodiments described above, properties that have been shown to influence performance include compliance, a low coefficient of friction, and in some cases elasticity. It is understood that not all of these need to be optimized, and there may be other properties that can be controlled to achieve a desired result.

In some embodiments the filament has a degree of deformability and elasticity that allows it to be pulled from the plunger and seal the leak. In some particular embodiments expanded PTFE, an expanded Teflon material, is used. In some embodiments the filament comprises an open cell foam.

For example, a low durometer open cell silicone foam with a single strand form can be used in both the straight out method (e.g., FIGS. 8A-8C) and roll out methods (e.g., FIGS. 5A-5C). In some embodiments PVA bio-absorbable type foams that provide good open cell performance can also be used. In some embodiments light wall (e.g., 0.004 in) low durometer (e.g., 20-35 shore A) silicone tubing can be used, particularly with the roll-out method. In some embodiment electro-spun or non-woven materials are used, and materials that allow for compaction of the mat under low pressures can be used in a straight out method with a relatively large cross section. It is understood that other suitable materials can be used to accomplish the intended goal.

The filaments can be further manipulated to control the performance characteristics. For example, one or more slits formed in the filament can provide desired functionality. Radial and axial slits have been shown to increase compliance and bending of the filament to optimize sealing performance to the lens. One or more slits can be formed in the filaments. The one or more slits can take on any configuration within the material.

In some embodiments the filament is a monofilament ePTFE material. The material can be formed with one or more loops (see FIGS. 6A-7B), and in some embodiments between one and three loops to optimize cross section in the plunger lumen relative to the tip plunger lumen size.

While specific embodiments have been described herein that focus on the use of a filament, other material can be incorporated into the delivery device to accomplish the goal. For example, any suitable material that can be used to seal off the gaps can be used. Other deformable or flexible materials, for example, that are not described herein could theoretically be suitable or adapted to function as a sealing element as described herein.

In alternative embodiments, the sealing element is a sealed porous tube of PTFE that is filled with viscoelastic or other fluid. The porous tube is adapted to allow viscoelastic to pass through the tube, or "weep" through the pores. In this alternative all of the viscoelastic fluid delivered into the system is pushed through the porous tube. The tube is adapted to seal off the fluid leaks as described above. The pore size can be varied to control the flow rate. Additionally, different viscoelastic fluids have different viscosities and flow properties, and thus the fluid can be varied to modify the flow rate as well.

FIGS. 11A-11C and 12A and 12B illustrate an embodiment that includes a plug component that is a flexible porous tube 200 sealed on its distal end. The tube is sheathed over a hypo-tube support 202 that is sealed to the interior lumen of the proximal end of the plunger 204. The porous tube 200 is long relative to the length of the support tube 202 to be able to extend to the tip of the cartridge when deployed. In a packaged state, the porous tube 200 is packed onto the support 202 to decrease the length. The support tube 202 communicates with the proximal end 206 of the plunger to allow for the passage of viscoelastic (not shown) to be delivered directly to the tip 208 of the sealed porous tube 200. With flow of viscoelastic through support tube 202 and into the porous tube 200, the porous tube 200 will pressurize slightly and extend off of the support tubing 202 to move into a region behind the lens that both seals, as described above, and is able to transmit axial force mechanically to the lens. When the lens moves forward in the tapering cartridge and creates an efficient seal, the sealing and mechanical action of the porous tube will lend less influence to its functionality and it will transition in performance to simply pass viscoelastic therethrough (via the pores), which will move the lens forward with pressure differential. The functionality of the porous tubing can be modified as needed by modifying the properties of the tubing. For example, with a low porosity (i.e., small pore size) material, the tube will generally develop a higher internal pressure while the viscoelastic tubing is flowing, which will allow it to function more as a mechanical hydraulic piston applying force to the lens when contacted. With a relatively higher porosity construction (i.e., larger pore size), the tube will behave more similarly to the filament structures described above, acting more prominently as a sealing element to seal off any leaking fluid. The porosity (or other property of the tube) can therefore be modified as needed to achieve the desired functionality of the porous tubing.

Figure 13A:
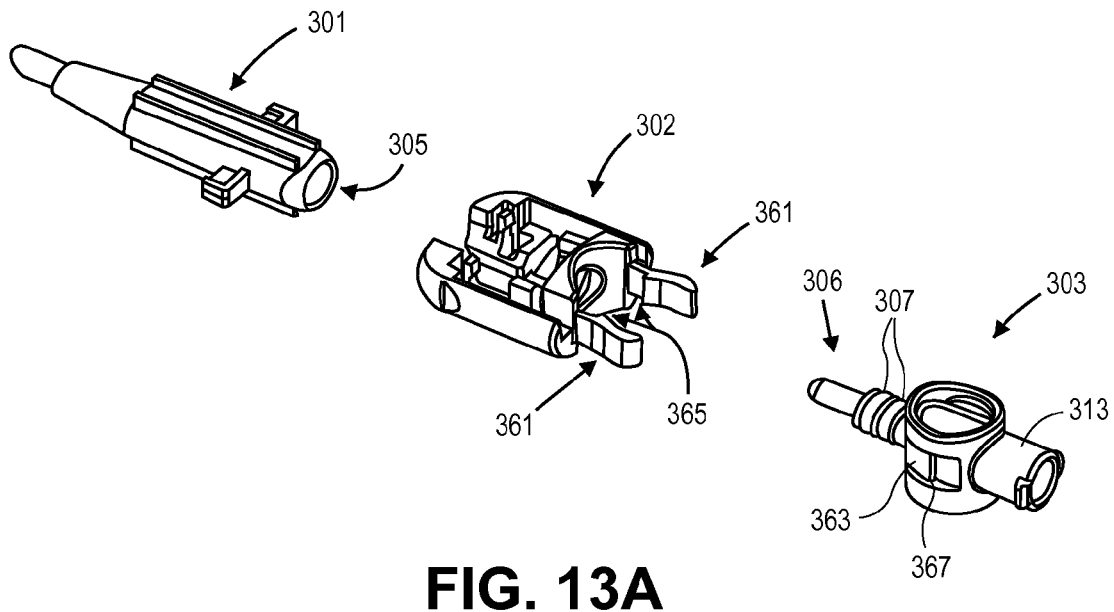
FIGS. 13A and 13B illustrate an exemplary intraocular lens delivery device with a sealing, or plugging, element.
Figure 13B:
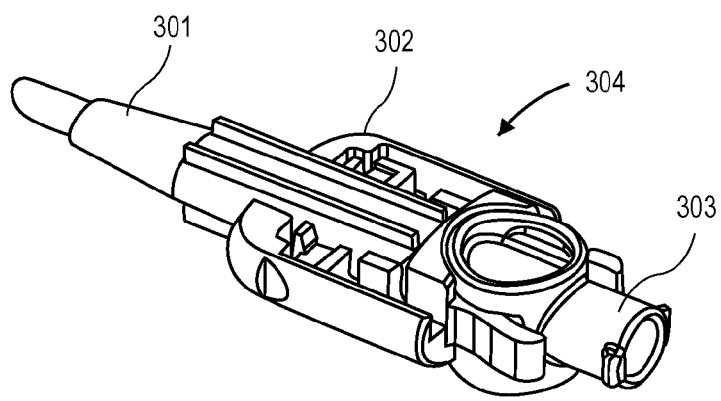

FIGS. 13A and 13B illustrate an alternative exemplary embodiment of an IOL delivery system adapted to deliver an IOL into an eye of a patient. The system includes cartridge 301, tray 302, and plunger 303. FIG. 13B shows the assembled system, which FIG. 13A shows the disassembled system components. In other embodiments one or more of the three components may be integrally formed rather than separate parts.

In the assembly of FIG. 13B, cartridge 301 is positioned with respect to tray 302 such that cartridge 301 and tray 302 are in secured engagement. In some embodiments cartridge 301 and tray 302 are integrally formed such that cartridge 301 is not adapted to be disassociated from tray 302. Tray 302 is adapted to receive a distal portion of plunger 303 therein. The distal end 306 of plunger 303 is sized and configured to be disposed within proximal opening 305 in cartridge 301 when assembled. Plunger 303 includes seals 307 in the form of O-rings. Seals 307 are adapted to create a seal between an inner surface of cartridge 301 when distal portion 306 of plunger is advanced into opening 305 of cartridge 301. Tray 302 facilitates the interaction between the cartridge and the plunger.

Plunger 303 has a proximal portion that is adapted to interact with a fluid delivery device, such as a syringe, so that fluid can be advanced from the fluid delivery device and into an inner lumen within plunger 303. Distal end 306 of plunger 303 is disposed within the cartridge, and thus the fluid is delivered to a location that is radially and axially within the lumen, even if it does not exit the plunger.

Cartridge 301 and tray 302 are in secure engagement as described in U.S. application Ser. No. 13/427,617, filed Mar. 22, 2012, which is incorporated by reference herein. Tray 302 includes two clips 361 with locking elements 365, wherein the clip are adapted to interface with camming surfaces 363 on plunger. Clips will splay outward as plunger 303 is advanced in tray 302, and locks 367 on plunger will lock with locks 365 on tray 302.

Figure 14A:
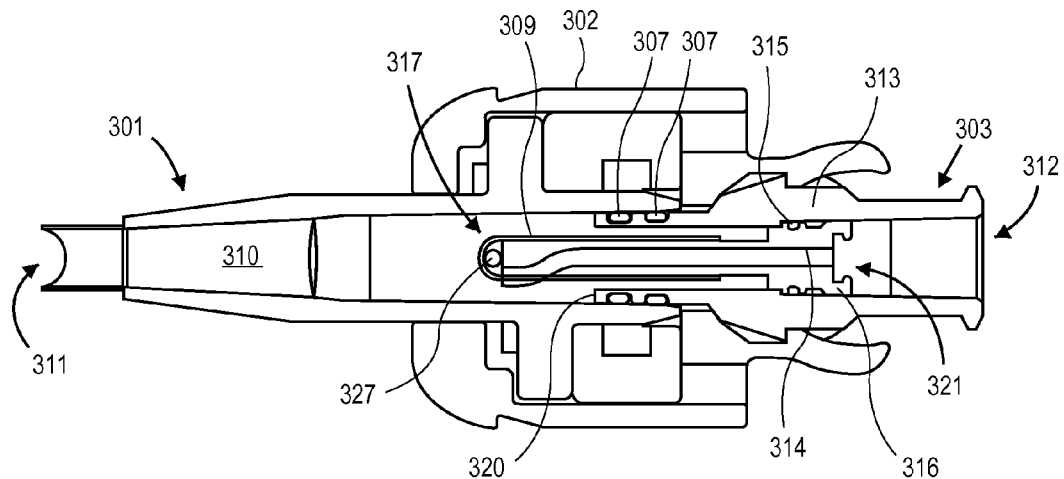
FIGS. 14A-14B illustrate an exemplary intraocular lens delivery device with a sealing, or plugging, element in a loaded configuration.
Figure 14B:
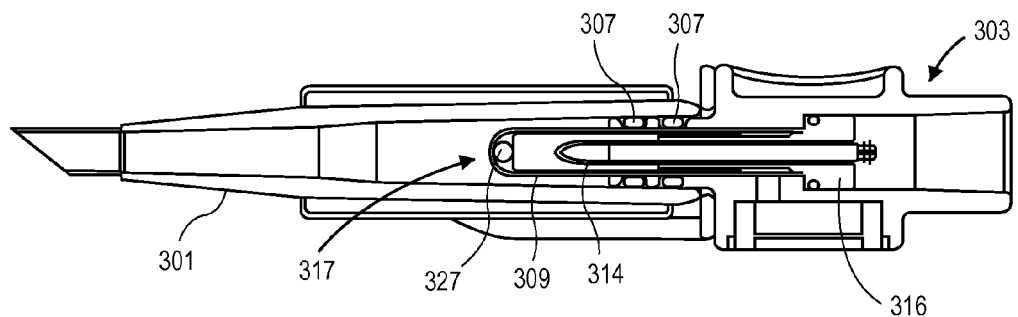

FIGS. 14A and 14B illustrate top section views of the assembled system from FIG. 13B (IOL not shown for clarity). As can be seen, the distal portion 306 of plunger 303 is disposed within a proximal portion of lumen 310 of cartridge. While not shown, an IOL will also be disposed within lumen 310 and positioned to be deployed out of the distal end 311 of cartridge 301.

Plunger 303 includes outer shell 313, on which seals 307 are disposed. As can be seen, seals 307 create a seal between outer shell 313 and an inner surface of lumen 310. Plunger 303 also includes plug subassembly 321 within a lumen of plunger 303. The plug subassembly is also shown in greater detail in FIG. 15. Plug subassembly 321 includes support tube base 316, in which support tube 314 is disposed and secured thereto, and plug element 317. Plug element 317 is sheathed over and secured to the outer surface of support tube 314 at location 308 (see FIG. 15). In one embodiment a heat shrunk collar secures plug element 317 to support tube 314 at location 308. The distal end of support tube 314 extends from the distal end of base 316, and is configured with an orientation to one side. That is, the distal portion of tube 314 does not extend along the longitudinal axis of plunger 303. This helps direct support tube 314 and plug 317 away from the trailing haptic. Plug element 317 is long relative to the length of the support tube 314 such that the distal end of plug element 317 is disposed at the tip of the cartridge when the plug is fully deployed. In a packaged, or loaded, state (see FIGS. 14A and 14B), plug element 317 is packed onto support tube 314 to decrease its relative length. Support tube 314 communicates with the proximal end of plunger 303 to allow for the passage of a fluid such as viscoelastic (not shown) into plug element 317. Plug subassembly 321 also include seal 315 adapted to create a seal between plug subassembly 321 and an inner surface of outer shell 313 of plunger 313.

In this embodiment, plug element 317 is a tubular structure secured to the distal end of support tube 314 as shown in FIG. 15. In this embodiment plug element is a flexible and porous material but need not necessary be porous. In one exemplary embodiment plug element is tubular ePTFE. In this embodiment the tubing is open-ended at both ends and is tied in a knot 327 along its length, with distal section 309 of plug 317 extending distally from knot 327. Knot 327 acts as a flow restrictor, and also helps stabilize the plug on the support tube. In this embodiment plug element 317 includes one or more optional perforations 325 just proximal to knot 327. The flow restrictor can be, for example, tied, glued, crimped, or swaged.

To load the plug subassembly into outer shell 313, distal section 39 of plug element 317 is rolled back, or folded back, towards the proximal end of the subassembly, in the direction of arrows shown in FIG. 15. It is everted until flow restrictor 307 is substantially at the distal end of the plug element 317. The distal portion of plug element 317, in a loaded configuration, thus has an everted section of material at its distal end. Plug assembly 321 is then advanced distally through open end 312 of outer shell 313 of plunger 303 until it is in the loaded position shown in FIGS. 14A and 14B. The open distal end of plug element 317, in its everted configuration, is retained within the lumen of outer shell 313, maintaining the eversion. FIG. 14A illustrates the biased configuration of the distal end of support tube 314. FIG. 14B is a side section view of the plug subassembly in a loaded configuration and position within outer shell 313 of plunger 303.

Figure 16A:
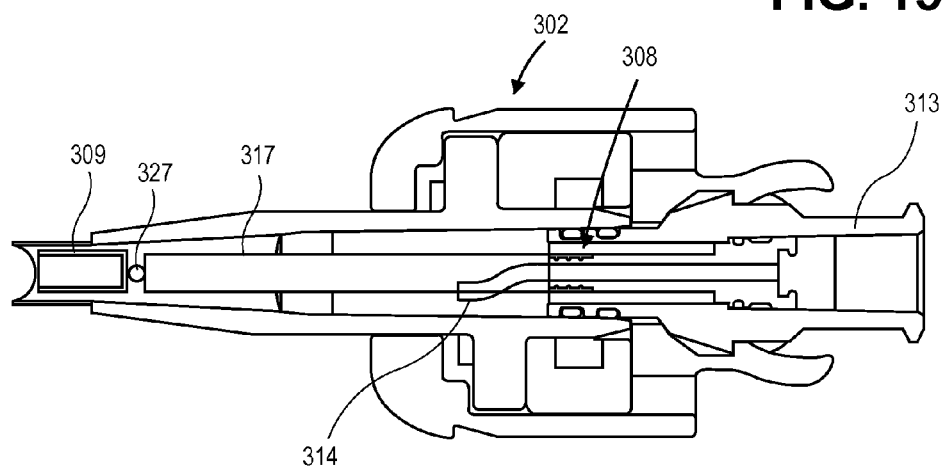
FIGS. 16A-16B illustrate an exemplary intraocular lens delivery device with a sealing, or plugging, element in a deployed configuration.
Figure 16B:
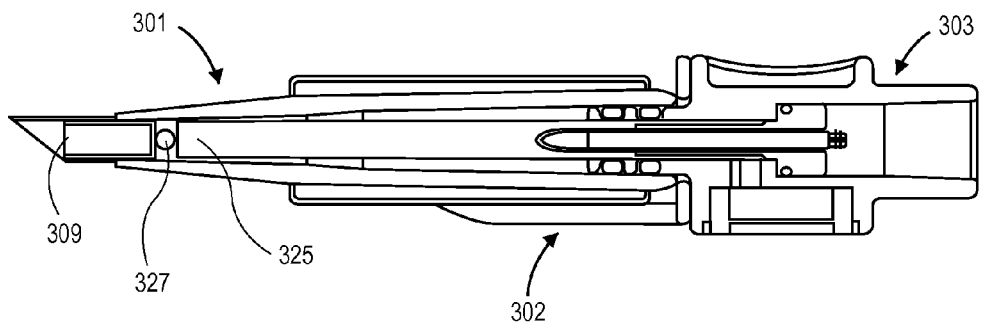

FIGS. 16A and 16B illustrate a fully deployed configuration of plug element 317 within cartridge 301, as is also shown in FIG. 15 outside of a cartridge. For clarity, this is illustrated without showing the IOL. A method of use with an IOL is shown below. As described in more detail below, after the plug is loaded (as shown in FIGS. 14A and 14B), a fluid is delivered through support tube 314 to initiate the deployment of plug element 317. As plug element 317 continues to be deployed, the everted section 309 remains everted until the full extension of the proximal portion of the plug element 317, at which time everted section 309 begins to unroll, and ultimately plug element 317 assumes the general elongate configuration shown in FIGS. 16A and 16B. The distal end of plug element 317 is substantially at the tip of cartridge 301 when fully deployed.

Figure 17A:
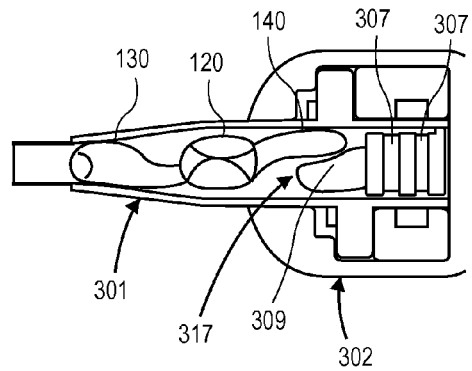
FIGS. 17A-E illustrate an exemplary delivery process of an intraocular lens with a delivery device with a plugging element.
Figure 17B:
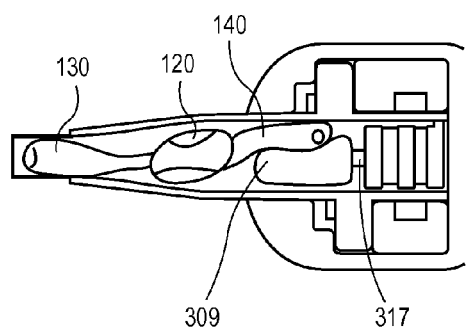

FIG. 17A illustrates an IOL comprising optic 120 and haptics 130 and 140 positioned (e.g., such as the IOL shown in FIG. 1) within cartridge 301. The IOL has been loaded into cartridge 301, and exemplary methods of loading the IOL into cartridge are described below. The disclosure herein is not intended to be limited to the manner in which IOL becomes positioned into cartridge 301. In the IOL's loaded configuration shown in FIG. 17A, leading haptic 130 has been reoriented from an at-rest orientation (see FIG. 1) and extends distally from optic 120. Trailing haptic 140 has also been reoriented from an at-rest orientation (see FIG. 1) and extends relatively proximally from optic 120 within cartridge.

In general, the delivery of the IOL out of the cartridge relies on development of a pressure differential in the cartridge to move the IOL distally through the cartridge and into the eye. The configuration of the IOL in general and/or the configuration that the IOL assumes when loaded into the cartridge, however, creates some gaps between the IOL and the inner surface(s) of the cartridge. That is, the IOL does not occupy the entire volume defined by the inner surfaces of the cartridge. The gaps, or voids, provide a path for some of the fluid to leak past the optic portion as fluid is advanced during the delivery. Ideally, none (or substantially none) of the fluid flows past the optic body portion. Ideally, all, or substantially all, of the fluid remains proximal to at least the optic body portion, building up pressure and forcing the IOL to be deployed out of the distal end of the cartridge. When fluid does flow past the lens body it can create drag on leading haptic 130 that is efficiently filling the tip of the cartridge. The advancing leading haptic can create a high strain at the connection between the leading haptic and the optic body, possibly causing damage at the connection point. Any IOL that may be susceptible to damage while being delivered may benefit from the systems and methods described herein.

An exemplary method of assembling the system includes placing cartridge 301 in tray 302, loading the IOL into cartridge 301, and then positioning plunger 303 relative to tray 302 such that it extends into cartridge 301, as shown in FIG. 17A. In FIG. 17A, plug subassembly 321 is in the same loaded position and configuration within cartridge 301 as shown in FIGS. 14A and 14B. In this configuration the plug element 317, and specifically everted portion 309, is positioned adjacent trailing haptic 140. Plug element 317 is disposed in a gap that exists between trailing haptic 140 and the inner surface of cartridge 301. As described above, this distal end of support tube 314 is oriented away from trailing haptic 140, which disposes the plug element 317 in the position shown in FIG. 17A, which is radially adjacent to trailing haptic 140. The support tube distal end is therefore adapted to avoid damaging the IOL when positioned in the cartridge. In this configuration plug element 317 acts like a plug to fill in the gap, or a substantial portion of the gap, to obstruct the flow of fluid, thereby minimize the amount of fluid that flows past the trailing haptic 140 during the delivery. Plug element 317 may or may not be in contact with the IOL at this time. As described below, plug element 317 reduces the volume of fluid that flows past the optic during delivery, increasing the pressure differential, and thus reducing the risk of damage to the lens. Plug element 317 can also be thought of as creating a seal, or a substantial seal, behind the IOL body to reduce the flow of viscoelastic around the IOL. "Plug" or "seal" are not limited to mean a completely fluid tight seal is created. These terms are used herein to mean that fluid flow around the IOL is reduced from what it would be without the plug or seal element. The plug element can also be any of the components described above as creating a seal behind the optic.

After the plug subassembly is positioned as shown in FIG. 17A, a fluid, such as a viscoelastic, is advanced through support tube 314 using a fluid delivery device such as a syringe (not shown). With the flow of viscoelastic through support tube 314 and into plug element 317, plug element 317 will pressurize slightly and reconfigure off of the support tube 314 to move more fully into a region behind the lens that plugs the gap and is able to transmit force mechanically to the lens.

As the IOL moves forward in the tapering cartridge inner lumen and creates an efficient, or substantial, seal, the sealing and mechanical action of the porous tube will lend less influence to its functionality and it will transition in performance to pass viscoelastic therethrough (via the pores, or other perforation constructs), which will move the lens forward with pressure differential. The functionality of the porous tubing can be modified as needed by modifying the properties of the tubing. For example, with a low porosity (i.e., small pore size) material, the tube will generally develop a higher internal pressure while the viscoelastic is flowing, which will allow it to function more as a mechanical hydraulic piston applying force to the lens when contacted. With a relatively higher porosity construction (i.e., larger pore size), the tube will behave more similarly to the filament structures above, acting more prominently as a plug element to seal off leaking fluid. The porosity (or other property of the tube) can therefore be modified as needed to achieve the desired functionality of the plug element.

As the fluid exists the distal end of support tube 314, the fluid pressure within the everted portion 309 of plug element 317 causes the distal end of plug element 317 to be released from the distal end of outer shell 313 of plunger 303. As the free distal end of the plug is released from the inner lumen of the plunger, it begins to at least partially seal against the inner walls of the cartridge, further reducing the volume of fluid that flows past the IOL. The plug element also at least partially plugs the gap that exists radially between adjacent trailing haptic 140 and the inner wall of the cartridge. This plugging action minimizes the volume of fluid that can flow past trailing haptic and therefore past optic portion, increasing the pressure differential in the cartridge.

Figure 17C:
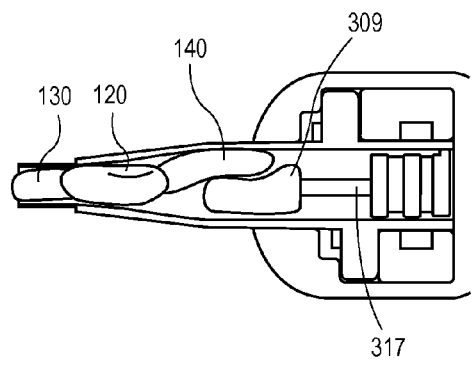
Figure 17D:
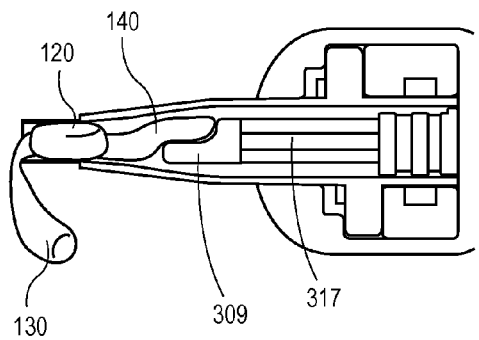
Figure 17E:
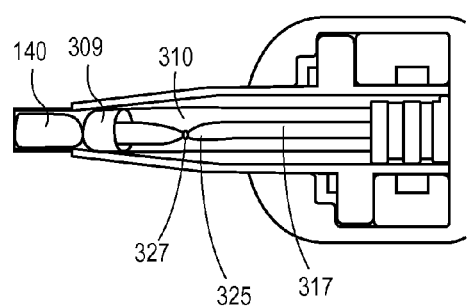

As fluid continues to be advanced through support element 314, as shown in FIG. 17C, the everted plug element continues to follow the IOL, still plugging the gap between trailing haptic 140 and the cartridge. As the optic is advanced closer to the distal port, as shown in FIG. 17D, the size of the port and the volume that the optic occupies cause the optic to begin to self-seal, or substantially create a seal in the distal port. In FIG. 17D the IOL begins to move distally relative to plug element 317, or outrun the plug element 317. In FIG. 17E the optic has been delivered out of the cartridge and trailing haptic 140 is rolling off of everted portion 309. This causes the everted portion of the plug element to unroll, as shown in FIG. 17E. The everted portion 309 of the plug element reduces drag on trailing haptic 140 between at least FIGS. 17D and 17E, when it is unfurling, or unrolling. A static plug element, unlike everted portion 309, can cause the trailing haptic to get stuck against the wall of the cartridge due to the radial expansion of the plug and static friction between the plug and the haptic. When the plug element includes a feature that can contact and unfurl with the trailing haptic, drag on the trailing haptic is reduced, preventing it from sticking against the cartridge wall and not deploying properly. This also reduces the likelihood of damage at the junction between the optic and the trailing haptic.

In the embodiment in FIGS. 17A-17E, plug 317 is a porous ePTFE material. The porous material is adapted to allow viscoelastic to pass through the tube, or "weep" through the pores. In embodiments herein plug 317 also includes optional perforations 325 (two shown in the embodiment in FIGS. 17A-17E) in the plug material just proximal to the knot location 327. In one particular embodiment the perforations are created with a 32 G surgical needle about 1 mm proximal to the knot. The perforations act as an over-pressure relief for the viscoelastic material (or other fluid). The porosity of the ePTFE (or other porous material) can be variable, and in some cases, which may depend on the viscoelastic material used, the material may fully contain the viscoelastic without allowing for effective weeping. If this occurs the plug element may disengage from the support tube 314 due to pressure at the end of extension. The perforations can thus serve as an over-pressure relief to prevent this possibility. In a secondary roll, the perforation can also direct fluid into the everted section of the plug to facilitate its release from the plunger and thus sealing against the inner surface of the cartridge.

The porosity of the plug allows viscoelastic to lubricate the interfaces between the moving plug and other system components. The porosity also allows the continued flow of the fluid when the plug is at full deployment and the IOL is moving due to a hydraulic seal at the tip.

The pore size can be varied to control the flow rate. Additionally, different viscoelastic fluids have different viscosities and flow properties, and thus the fluid can be varied to modify the flow rate as well. In an exemplary embodiment the plug element is ePTFE and the intermodal distance (i.e., the distance between the nodes), which determines the porosity, is 100 µm. ePTFE with other internodal distances can also be used.

Figure 18:
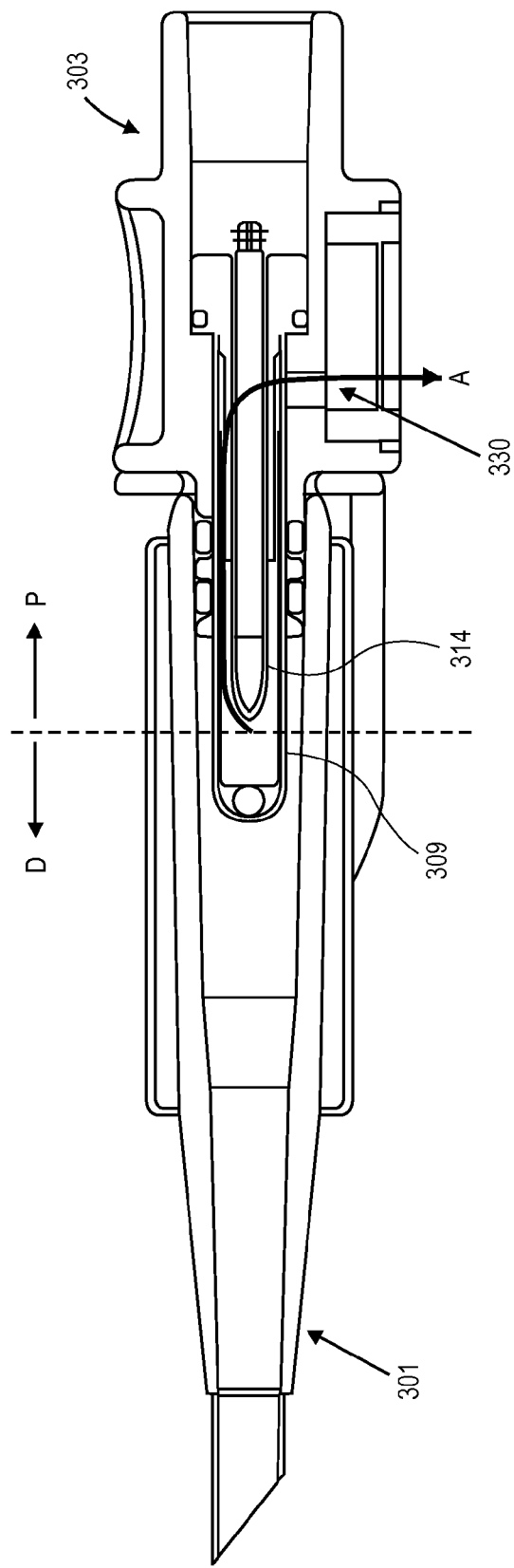
FIG. 18 illustrates venting of air out of a vent that is not a delivery port in an intraocular lens delivery device.

The embodiment shown in FIGS. 13A, 13B, 14A, 14B, 16A, 16B, and 17A-17E are also adapted to purge trapped air in the system that, if not purged, can interfere with the delivery process. FIG. 18 illustrates a side section view of the assembled device shown in FIG. 14B (IOL not shown for clarity), illustrating the purging of air from the plunger. As described herein, fluid travels from a syringe (not shown) through support tube 314 and exits in proximity of the trailing haptic of the IOL within the plug element (everted section 309 labeled). A fluid front travels both distally in the "D" direction shown, filling the plug element, and rearward in the "P" direction, which evacuates dead volume air through vent 330 in the direction of arrow "A." The vent will not pass viscoelastic so is able to maintain pressure when fully evacuated. This effect purges the air from the back of the system to reduce spring effects of trapped air during the release of the IOL during delivery. In some instances if the air is not purged the air can forcefully push the IOL forward during delivery, without operator action/input, possibly damaging the IOL or the capsule in the eye, and can even cause the IOL to be delivered outside of the capsule. The purging of air is important for a smooth, controlled delivery of the IOL. Some IOLs may not require as much control in the delivery, and thus venting of air may not be required.

In some embodiments the delivery system includes a vent and does not include a plug, or sealing element. In these embodiments fluid such as viscoelastic is delivered towards the lens as part of the delivery process. Air venting to increase control during delivery while decreasing the volume of air bubbles that are moved forward through the tip into the eye provides a significant advantage even in the absence of a plug element. In an alternative embodiment, the device is similar to the delivery device in FIGS. 14A and 14B but does not include a plug element 317.

Figure 19A:
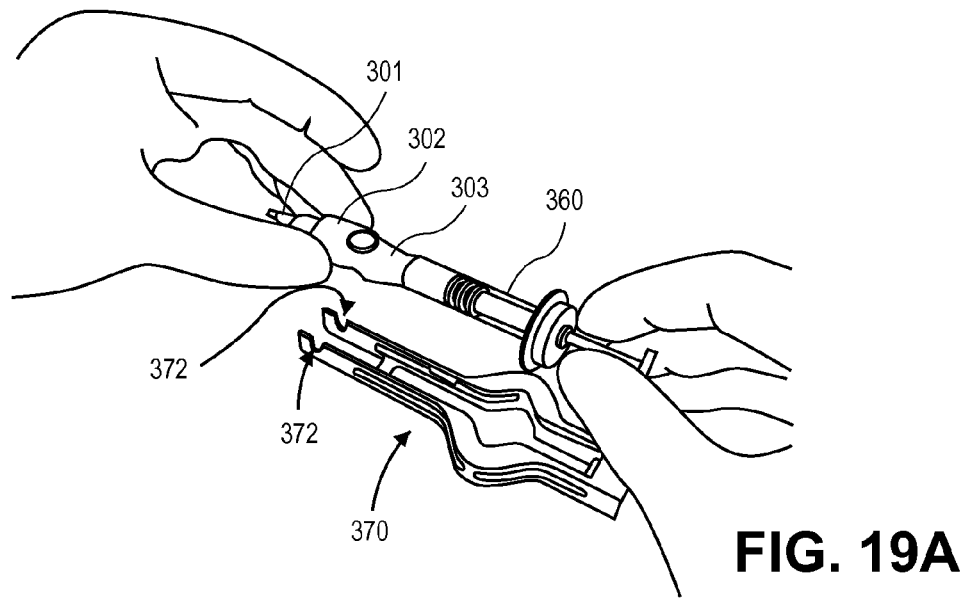
FIGS. 19A-19C illustrate an exemplary screw drive for advancing fluid through a an intraocular lens delivery device.
Figure 19B:
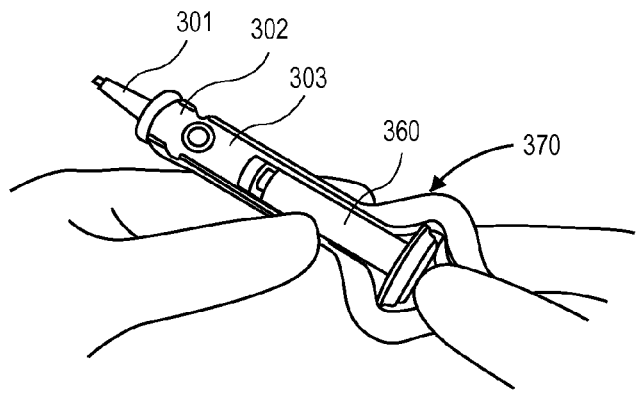
Figure 19C:
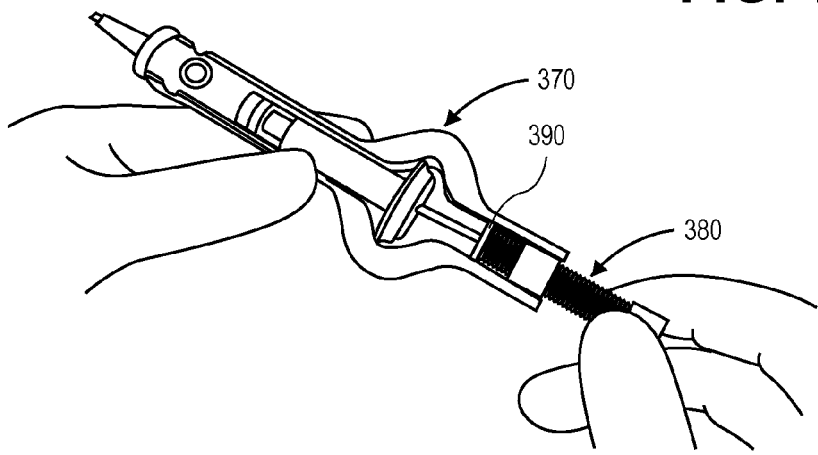

FIGS. 19A-19C illustrate an exemplary way of driving fluid such as viscoelastic from within a delivery device into the support tube 314. In this embodiment the delivery assembly, including cartridge 301, tray 302, and plunger 303, with syringe 360 secured thereto, are mounted into screwdrive assembly 370. Screwdrive assembly 370 includes base 390 with end posts 372 over which slots in tray 302 are aligned. The delivery assembly self-aligns with screw 380. Screw 380 is advanced until it touches the plunger of the syringe, as shown in FIG. 19C. Screw 380 is then turned to cause the syringe plunger to be advanced, which drives the fluid from the syringe and into support tube 314. The screwdrive assembly can be modified to more finely control the force applied to the syringe, and can include a pressure gauge.

As set forth herein, an IOL can be positioned, or loaded, into the cartridge using any suitable technique. For the specific IOL described herein, the loading process includes changing the orientation of the haptics with respect to the optic, such that the haptics generally extend away from the optic. In general this process of reorienting the haptics is referred to herein as splaying the haptics. The loading process, for the IOL herein, also includes reconfiguring at least one portion of the IOL, such as the optic. Exemplary loading techniques include without limitation, hydraulically loading the IOL, as is set forth in U.S. application Ser. No. 12/178, 565, filed Jul. 23, 2008. Alternatively, the IOL can be mechanically loaded, such as is described in U.S. application Ser. No. 13/427,617, filed Mar. 22, 2012. Another example of mechanical loading includes using forceps to pick up the IOL, reorient one or more haptics, and advance the IOL into the cartridge.

The IOL can be loaded into the cartridge and stored, such as for packaging, or loading can occur just prior to implantation.

The devices and methods herein are able to deliver an IOL through an incision that is between about 2.8 mm to about 4.5 mm. In some embodiments the incision is about 4 mm. The devices and methods can be modified if needed to deliver an IOL through a bigger or smaller incision.

While the disclosure focused on a tubular member for the plug, other sealing mechanisms can also be inserted into the cartridge to help create at least a partial seal between the IOL and cartridge to aid in the delivery of the IOL.

The IOL to be delivered need not have one or more dedicated "haptics" as described herein. The IOL can more generally include a peripheral portion.

What is claimed is:

1. A method of deploying an intraocular lens into an eye, comprising:
    providing an intraocular lens within a delivery lumen;
    at least partially plugging a gap with a delivery device plugging element between the intraocular lens and an inner surface of the delivery lumen; and
    delivering a fluid into the delivery lumen to deploy the intraocular lens from the delivery lumen and into an eye.

2. The method of claim 1 wherein at least partially plugging a gap reduces the amount of fluid that flows past the intraocular lens in the delivery lumen.

3. The method of claim 1 wherein at least partially plugging a gap allows for an increase in fluid pressure in the delivery lumen proximal to an optic portion of the intraocular lens.

4. The method of claim 1 wherein at least partially plugging a gap increases a pressure differential in the delivery lumen between a location proximal to an optic portion of the intraocular lens and a location distal to the intraocular lens.

5. The method of claim 1 wherein at least partially plugging a gap comprises at least partially plugging a gap that is disposed radially between the intraocular lens and an inner surface of the delivery lumen.

6. The method of claim 1 wherein at least partially plugging a gap between the intraocular lens and an inner surface of the delivery lumen comprises at least plugging a gap that exists between a trailing haptic and an inner surface of the delivery lumen.

7. The method of claim 1 further comprising reconfiguring the plugging element while delivering the fluid into the delivery lumen.

8. The method of claim 7 wherein reconfiguring the plugging element acts to form a seal between the plugging element and an inner surface of the delivery lumen.

9. The method of claim 7 wherein reconfiguring the plugging element unrolls the plugging element.

10. The method of claim 1 wherein the gap is part of a fluid flow path through which fluid can flow from a location proximal to an optic portion of the intraocular lens to a location distal to the optic portion of the intraocular lens.

11. A method of deploying an intraocular lens into an eye, comprising:
    providing an intraocular lens within a delivery lumen;
    at least partially plugging a gap between the intraocular lens and an inner surface of the delivery lumen; and
    delivering a fluid into the delivery lumen to deploy the intraocular lens from the delivery lumen and into an eye, wherein delivering a fluid into the delivery lumen to deploy the intraocular lens from the delivery lumen comprises delivering a fluid through a porous material.

12. A method of deploying an intraocular lens into an eye, comprising:
    providing an intraocular lens within a delivery lumen;
    at least partially plugging a gap disposed radially between the intraocular lens and an inner surface of the delivery lumen; and
    delivering a fluid into the delivery lumen to deploy the intraocular lens from the delivery lumen.

13. The method of claim 12 wherein at least partially plugging a gap disposed radially between the intraocular lens and an inner surface of the delivery lumen comprises at least partially plugging a gap disposed radially between a haptic extending generally longitudinally through the delivery lumen and in inner surface of the delivery lumen.

14. An apparatus for deploying an intraocular lens into an eye, comprising:
    an intraocular lens delivery lumen with an intraocular lens disposed therein;
    a support device adapted to be disposed within the delivery lumen, the support device having a lumen therein adapted to allow a fluid to flow therethrough; and
    a plug element disposed relative to the support device such that it is adapted to at least partially plug a gap between an intraocular lens positioned in the delivery lumen and an inner surface of the delivery lumen, wherein the apparatus does not comprise the intraocular lens.

15. The apparatus of claim 14 wherein the support device is secured to the plug element.

16. The apparatus of claim 15 wherein the plug element has a proximal portion secured to the support device.

17. The apparatus of claim 14 wherein the plug element is a tubular element.

18. The apparatus of claim 17 wherein the plug element is open at a distal end after deployment.

19. The apparatus of claim 17 wherein the plug element has a fluid flow restriction proximal to a distal end of the plug element.

20. The apparatus of claim 14 wherein the plug element is everted at a distal end.

21. The apparatus of claim 14 wherein the plug element is flexible.

22. The apparatus of claim 14 wherein the plug element is adapted to be reconfigured in response to fluid flow through the lumen.

23. The apparatus of claim 22 wherein only a distal portion of the plug element is adapted to be reconfigured.

24. The apparatus of claim 14 wherein the plug element has a flow restriction proximal to a distal end of the plug element.

25. The apparatus of claim 24 wherein the flow restriction is a tied off section of the plug element.

26. The apparatus of claim 24 wherein the plug element has portion distal to the flow restriction that is adapted to be reconfigured.

27. The apparatus of claim 14 wherein the plug element is open at a distal end.

28. The apparatus of claim 14 wherein the plug element is an ePTFE tube.

29. The apparatus of claim 14 wherein a distal portion of the support element is oriented towards an inner wall of the delivery lumen.

30. The apparatus of claim 14 wherein a distal portion of the support element is oriented away from a longitudinal axis of a proximal portion of the support element.

31. The apparatus of claim 14 wherein a trailing haptic extends proximal relative to an optic portion of the intraocular lens.

32. The apparatus of claim 31 wherein the plug element is disposed radially between the intraocular lens and an inner surface of the delivery lumen.

33. The apparatus of claim 14 further comprising a vent adapted to vent air from inside the apparatus.

34. An apparatus for deploying an intraocular lens into an eye, comprising:
   an intraocular lens delivery lumen with an intraocular lens disposed therein;
   a support device adapted to be disposed within the delivery lumen, the support device having a lumen therein adapted to allow to fluid to flow therethrough; and
   a plug element disposed relative to the support device such that it is adapted to at least partially plug a gap between an intraocular lens positioned in the delivery lumen and an inner surface of the delivery lumen,
   wherein the plug element is porous.

35. An apparatus for deploying an intraocular lens into an eye, comprising:
   an intraocular lens delivery lumen and an intraocular lens disposed therein;
   a support device adapted to be disposed within the delivery lumen, the support device having a lumen therein adapted to allow a fluid to flow therethrough; and
   a flexible plug element secured to the support device, the plug element adapted to at least partially plug a gap between an intraocular lens positioned in the delivery lumen and an inner surface of the delivery lumen when fluid is flowed into the lumen, wherein the plug element does not include the intraocular lens.

* * * * *